(12) United States Patent
Vunjak-Novakovic et al.

(10) Patent No.: US 9,958,436 B2
(45) Date of Patent: May 1, 2018

(54) DETERMINATION OF CELL CHIRALITY

(75) Inventors: Gordana Vunjak-Novakovic, New York, NY (US); Leo Qun Wan, Watervliet, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 1029 days.

(21) Appl. No.: 14/126,902

(22) PCT Filed: Jun. 15, 2012

(86) PCT No.: PCT/US2012/042712
§ 371 (c)(1),
(2), (4) Date: Sep. 12, 2014

(87) PCT Pub. No.: WO2012/174404
PCT Pub. Date: Dec. 20, 2012

(65) Prior Publication Data
US 2015/0004643 A1    Jan. 1, 2015

Related U.S. Application Data

(60) Provisional application No. 61/498,469, filed on Jun. 17, 2011, provisional application No. 61/498,475, filed on Jun. 17, 2011.

(51) Int. Cl.
*G01N 33/50* (2006.01)
*C12N 5/00* (2006.01)

(52) U.S. Cl.
CPC ....... *G01N 33/5091* (2013.01); *C12N 5/0068* (2013.01); *C12N 2503/00* (2013.01); *C12N 2535/10* (2013.01)

(58) Field of Classification Search
None
See application file for complete search history.

(56) References Cited

U.S. PATENT DOCUMENTS

| 5,470,739 A | 11/1995 | Akaike et al. |
| 2003/0228038 A1 | 12/2003 | Douglass et al. |
| 2016/0377603 A1* | 12/2016 | Wan .................. G01N 33/5091 435/34 |

OTHER PUBLICATIONS

Thery et al. Anistropy of cell ahesive ... PNAS vol. 103(52). 2006. 19771-19776.*
Adams et al., Early, H+-V-ATPase-dependent proton flux is necessary for consistent left-right patterning of non-mammalian vertebrates, Development, 2006, pp. 1657-1671, vol. 133, No. 9.
Afzelius, A Human Syndrome Caused by Immotile Cilia, Science, 1976, pp. 317-319, vol. 193.
Aylsworth, Clinical Aspects of Defects in the Determination of Laterality, Am J Med Genet, 2001, pp. 345-355, vol. 101, No. 4.
Brown et al., The development of handedness in left/right asymmetry, Development, 1990, pp. 1-9, vol. 109.
Bubb et al., Effects of Jasplakinolide on the Kinetics of Actin Polymerization. An Explanation for Certain In Vivo Observations, J Biol Chem., 2000, pp. 5163-5170, vol. 275, No. 7.
Chen et al., Geometric Control of Cell Life and Death, Science, 1997, pp. 1425-1428, vol. 276.
Cooper, Effects of Cytochalasin and Phalloidin on Actin, J Cell Biol., 1987, pp. 1473-1478, vol. 105.
Coue et al., Inhibition of actin polymerization by latrunculin A, FEBS Lett., 1987, pp. 316-318, vol. 213, No. 2.
Derry et al., Substoichiometric Binding of Taxol Suppresses Microtubule Dynamics, Biochemistry, 1995, pp. 2203-2211, vol. 34, No. 7.
Desai et al., Cell polarity triggered by cell-cell adhesion via E-cadherin, J. Cell Sci., 2009, pp. 905-911, vol. 122, No. 7.
Edwards et al., The global trend in plant twining direction, Global Ecol. Biogeogr., 2007, pp. 795-800, vol. 16, No. 6.
Elhai et al., Conjugal Transfer of DNA to Cyanobacteria, Methods in Enzymology, 1988, pp. 747-754, vol. 167.
Herman, Actin isoforms, Curr. Opin. Cell. Biol., 1993, pp. 48-55, vol. 5, No. 1.
Hirokawa et al., Nodal Flow and the Generation of Left-Right Asymmetry, Cell, 2006, vol. 125, pp. 33-45.
Hozumi et al., An unconventional myosin in *Drosophila* reverses the default handedness in visceral organs, Nature, 2006, pp. 798-802, vol. 440.
International Search Report and Written Opinion dated Oct. 5, 2012 in corresponding International Application No. PCT/US2012/042712, 9 pages.
Irwin et al., Zinc—A Free Database of Commercially Available Compounds for Virtual Screening, J Chem Inf Model, 2005, pp. 177-182, vol. 45, No. 1.
Isemura et al., Myosin Light Chain Kinase Inhibitors ML-7 and ML-9 Inhibit MouseLung Carcinoma Cell Attachment to the Fibronectin Substratum, Cell Biol Int Rep, 1991, pp. 965-972, vol. 15, No. 10.
Ishizaki et al., Pharmacological Properties of Y-27632, a Specific Inhibitor of Rho-Associated Kinases, Mol Pharmacol, 2000, pp. 976-983, vol. 57.
Itasaki et al., Actin bundles on the right side in the caudal part of the heart tube play a role in dextro-looping in the embryonic chick heart, Anat. Embryol., 1991, pp. 29-39, vol. 183, No. 1.
Karlon et al., Measurement of Orientation and Distribution of Cellular Alignment and Cytoskeletal Organization, Ann. Biomed. Eng., 1999, pp. 712-720, vol. 27, No. 6.
Kovacs et al., Mechanism of Blebbistatin Inhibition of Myosin II, J Biol Chem., 2004, pp. 35557-35563, vol. 279.
Levin et al., The compulsion of chirality: toward an understanding of left-right asymmetry, Genes Dev, pp. 763-769, vol. 12.
Levin et al., Asymmetries in $H^+/K^+$-ATPase and Cell Membrane Potentials Comprise a Very Early Step in Left-Right Patterning, Cell, 2002, pp. 77-89, vol. 111.

(Continued)

*Primary Examiner* — Blaine Lankford
(74) *Attorney, Agent, or Firm* — Reed Smith LLP; Lisa A. Chiarini; Matthew S. Gibson

(57) ABSTRACT

Methods for determining cell chirality using micropatterned substrates are disclosed. Also provided are methods for diagnosing diseases such as genetic diseases or cancer by comparing the chirality of sample cells from a subject with normal cells, and determining a difference in chirality between the sample cells and normal cells.

6 Claims, 11 Drawing Sheets

(56) References Cited

OTHER PUBLICATIONS

Levin, Left-right asymmetry in embryonic development: a comprehensive review, Mech Dev, 2005, vol. 122, pp. 3-25.
Li et al., Symmetry Breaking in Biology, Cold Spring Harb Perspect Biol, 2010, pp. 1-5, vol. 2, No. a003475.
Lipinski, Drug-like properties and the causes of poor solubility and poor permeability, J. Pharm. Tox. Methods, 2000, pp. 235-249, vol. 44.
Mercola et al., Left-right Asymmetry Determination in Vertebrates, Annu Rev Cell Dev Biol, 2001, pp. 779-805, vol. 17.
Okada et al., Mechanism of Nodal Flow: A Conserved Symmetry Breaking Event in Left-Right Axis Determination, Cell, 2005, pp. 633-644, vol. 121.
Pohl et al., Chiral forces organize left-right patterning in C. elegans by uncoupling midline and anteroposterior axis, Dev. Cell, Bol., 2010, pp. 402-412, vol. 19, No. 3.
Shibazaki et al., Body handedness is directed by genetically determined cytoskeletal dynamics in the early embryo, Curr. Biol., 2004, pp. 1462-1467, vol. 14, No. 16.
Shimizu et al., Actin Concentration and Monomer-Polymer Ratio in Developing Chicken Skeletal Muscle, J. Biochem., 1986, pp. 751-759, vol. 99, No. 3.
Speder et al., Type ID unconventional myosin controls left-right asymmetry in *Drosophila,* Nature, 2006, pp. 803-807, vol. 440.
Speder et al., Strategies to establish left/right asymmetry in vertebrates and invertebrates, Curr Opin Genet Dev, 2007, pp. 351-358, vol. 17, No. 4.
Speder et al., Left-right asymmetry: class I myosins show the direction, Curr Opin Cell Biol, 2007, pp. 82-87, vol. 19, No. 1.
Studier, Protein production by auto-induction in high-density shaking cultures, Protein Expr Purif., 2005, pp. 207-234, vol. 41, No. 1.
Taber, Biophysical mechanisms of cardiac looping, Int. J. Dev. Biol., 2006, pp. 323-332, vol. 50, No. 2-3.
Tabin, The key to left-right asymmetry, Cell, 2006, pp. 27-32, vol. 127.
Teage et al., The design of Leadlike Combinatorial Libraries, Angewandte Chemie Int. Ed., 1999, pp. 3743-3748, vol. 38, No. 24.
Thery et al., Adhesive Micropatterns for Cells: A Microcontact Printing Protocol, Cold Spring Harb. Protoc., 2009, pp. 1-11, vol. 4, No. 7.
Wan et al., Geometric control of human stem cell morphology and differentiation, Integr. Biol., 2010, pp. 346-353, vol. 2, No. 0.
Wan et al., Micropatterned mammalian cells exhibit phenotype-specific left-right asymmetry, PNAS, 2011, pp. 12295-12300, vol. 108, No. 30.
Wan et al., Bioengineering approach to study cell chirality for in vitro diagnosis of disease, Proposal to RISE, Dec. 2010 (6 pages).
Xu et al., Polarity reveals intrinsic cell chirality, PNAS, 2007, pp. 9296-9300, vol. 104, No. 22.
Zhou et al., Subpixel displacement and deformation gradient measurement using digital image/speckle correlation (DISC), Opt. Eng., 2001, pp. 1613-1620, vol. 40, No. 8.

\* cited by examiner

A

Human primary fibroblasts

B fibroblast cell line from healthy skin

C fibroblast cell line from Basal cell carcinoma

DETERMINATION OF CELL CHIRALITY

CROSS-REFERENCE TO RELATED APPLICATIONS

The present application claims the benefit of priority to PCT International Application No. PCT/US12/42712 filed 15 Jun. 2012, which claims the benefit of priority to U.S. Provisional Application Ser. No. 61/498,469 filed on Jun. 17, 2011, and U.S. Provisional Application Ser. No. 61/498,475 filed on Jun. 17, 2011, each of which is incorporated herein by reference in its entirety.

STATEMENT REGARDING FEDERALLY SPONSORED RESEARCH OR DEVELOPMENT

This invention was made with government support under grant number R01 DE016525 awarded by National Institutes of Health NIH-NIDCR and grant number P41EB002520 awarded by National Institutes of Health NIH-NIBIB. The government has certain rights in the invention.

FIELD OF THE INVENTION

The present disclosure generally relates to cell chirality and analysis thereof.

BACKGROUND OF THE INVENTION

Detecting differences at the cellular level is an ongoing problem which, if successfully addressed, could help solve several prevalent ailments, including cancers and prenatal diseases.

Normal tissue function requires appropriate cell positioning and directional motion. This property, known as chirality, can be altered by genetic and environmental factors, leading to, for example, birth defects and tumor formation.

Current methods to diagnose cancer are based on biomarkers, imaging, and analysis of tissue specimens. In most cases, the findings from one assay (such as imaging) are corroborated by other assays (such as pathological evaluation of biopsy samples).

Chirality is often known as left-right (LR) asymmetry in the development of numerous living organisms, including climbing plants (1), helices of snail shells (2), and the human body (3, 6). Genetic diseases and prenatal exposure to teratogens (4) can cause birth defects in laterality. The LR asymmetry has been studied in animal embryos, which are difficult to control and are not necessarily representative of human condition (7, 8). Recent studies focused on directional nodal flow driven by primary cilia (9-11), pH gradients resulting from asymmetric expression of ion channels (12, 13), and asymmetric vesicular transport via myosin 1D along actin cable networks (14-16).

The initiation of chirality in development is often first observed in populations of cells of the same type, such as snail embryonic cells at 4-cell and 8-cell stages and mouse cells at embryonic nodes. The establishment of chirality within such cell clusters may rely on some intracellular structure, such as the hypothetical F-molecule or actin/microtubule cytoskeleton (17, 18) that can distinguish left from right by orienting the $3^{rd}$ axis with respect to predetermined dorsal-ventral and anterior-posterior axes. In addition, during development, the specification and self-organization of migrating cells are mediated by physical boundaries imposed by the extracellular matrix and the surrounding cells and tissues.

SUMMARY OF THE INVENTION

Among the various aspects of the present disclosure is the provision of a method for determining cell chirality based, at least in part, on the surprising discovery that directional cell movement on a micro-patterned substrate was significantly biased towards either left or right orientation (chirality) in a way that was specific to the cell phenotype. As described herein, cells cultured on micropatterns with defined appositional boundaries exhibit chiral morphogenesis that can be readily determined by analysis of cell alignment and directional motion. Directionality of cell alignment or motion can be according to measurement of a pattern of angular deviation from a reference.

One aspect provides a method for determining chirality of a cell. In some embodiments, the method includes culturing a cell on a micropatterned substrate and determining directionality of the cell proximal to a boundary of the micropatterned substrate.

In some embodiments, the micropatterned substrate comprises one or more of an x-axis, a y-axis, a path, an inner boundary, and an outer boundary. In some embodiments, the path of the substrate micropattern is at least partially or substantially parallel with the y-axis. In some embodiments, a surface of the path of the substrate micropattern is suitable for culture of the cell. In some embodiments, the inner boundary or the outer boundary is at least partially or substantially perpendicular to the x-axis.

In some embodiments, directionality of the cell comprises a leftward or a rightward migration of the cell over time. In some embodiments, directionality of the cell comprises a leftward or a rightward alignment of the cell.

In some embodiments, directionality of the cell is measured along the y-axis. In some embodiments, directionality of the cell is measured along the y-axis with respect to the x-axis. In some embodiments, directionality of the cell is measured along the y-axis with respect to the x-axis as measured from the path to the inner boundary along the x-axis. In some embodiments, directionality of the cell is measured along the y-axis with respect to the x-axis as measured from the path to the outer boundary along the x-axis. In some embodiments, directionality of the cell is measured along the y-axis with respect to the x-axis as measured from a nucleus of the cell to a centrosome of the cell along the x-axis. In some embodiments, directionality of the cell is measured along the y-axis with respect to the x-axis as measured from the nucleus of the cell to a Golgi apparatus of the cell along the x-axis.

In some embodiments, culturing the cell on the micropatterned substrate comprises culturing the cell on the micropatterned substrate for an amount of time sufficient for the cell to contact the inner boundary or the outer boundary.

In some embodiments, a plurality of cells are cultured on the micropatterned substrate. In some embodiments, a plurality of cells are cultured on the micropatterned substrate at a density of about 2,000 cells $cm^{-2}$ to about 500,000 cells $cm^{-2}$. In some embodiments, a plurality of cells are cultured on the micropatterned substrate at a density of about 20,000 cells $cm^{-2}$ to about 50,000 cells $cm^{-2}$. In some embodiments, a plurality of cells are cultured on the micropatterned substrate at a density of about 2,000 cells $cm^{-2}$; about 5,000 cells $cm^{-2}$; about 10,000 cells $cm^{-2}$; about 15,000 cells $cm^{-2}$; about 20,000 cells $cm^{-2}$; about 25,000 cells $cm^{-2}$; about 30,000 cells $cm^{-2}$; about 35,000 cells $cm^{-2}$; about 40,000 cells cm$^{-2}$; about 45,000 cells cm$^{-2}$; about 50,000 cells cm$^{-2}$; about 100,000 cells cm$^{-2}$; about 150,000 cells cm$^{-2}$; about 200,000 cells cm$^{-2}$; about 250,000 cells cm$^{-2}$; about 300,000 cells cm$^{-2}$; about 350,000 cells cm$^{-2}$; about 400,000 cells cm$^{-2}$; about 450,000 cells cm$^{-2}$; or about 500,000 cells cm$^{-2}$.

In some embodiments, a plurality of cells are cultured on the micropatterned substrate and mean directionality of migration of the cells is determined. In some embodiments, a plurality of cells are cultured on the micropatterned substrate and mean directionality of alignment of the cells is determined.

In some embodiments, the substrate micropattern, or a portion thereof, can have a ring, ring-like, linear, or semi-linear geometrical shape. In some embodiments, the substrate micropattern, or a portion thereof, can have a ring, has a ring or ring-like shape having an inner diameter of about 150 µm, about 200 µm, about 250 µm, about 300 µm, or about 350 µm. In some embodiments, the substrate micropattern, or a portion thereof, has an inner boundary and an outer boundary separated by a distance of about 100 µm, about 150 µm, about 200 µm, about 250 µm, or about 300 µm along the x-axis. In some embodiments, the above described inter-boundary distance is measured along the x-axis.

In some embodiments, determining directionality of alignment or migration of the cell occurs after the cell is in contact with the inner boundary. In some embodiments, determining directionality of alignment or migration of the cell occurs after the cell is in contact with the inner boundary. In some embodiments, determining directionality of alignment or migration of cells occurs after the cells are in contact with the inner boundary, the outer boundary, or the inner boundary and the outer boundary.

In some embodiments, directionality of alignment of the cell is the angular deviation of the cell away from the y-axis. In some embodiments, directionality of migration of the cell is the angular deviation of migration of the cell away from the y-axis. In some embodiments, determining directionality of alignment or migration of the cell includes determining an angular deviation of alignment or migration of the cell away from the y-axis.

In some embodiments, determining directionality of alignment of the cell includes determining an angular deviation of alignment of the cell away from the y-axis, where a positive angular deviation is classified as a counterclockwise (CCW) alignment and a negative angular deviation is classified as a clockwise (CW) alignment. In some embodiments, determining directionality of migration of the cell includes determining an angular deviation of migration of the cell away from the y-axis, where a positive angular deviation is classified as a counterclockwise (CCW) alignment and a negative angular deviation is classified as a clockwise (CW) alignment. In some embodiments, a positive angular deviation greater than about 2 degrees, about 3 degrees, about 4 degrees, about 5 degrees, about 6 degrees, about 7 degrees, about 8 degrees, about 9 degrees, about 10 degrees, about 11 degrees, about 12 degrees, about 13 degrees, about 14 degrees or about 15 degrees is classified as a counterclockwise (CCW) alignment. In some embodiments, a negative angular deviation less than about negative 2 degrees, about negative 3 degrees, about negative 4 degrees, about negative 5 degrees, about negative 6 degrees, about negative 7 degrees, about negative 8 degrees, about negative 9 degrees, about negative 10 degrees, about negative 11 degrees, about negative 12 degrees, about negative 13 degrees, about negative 14 degrees or about negative 15 degrees is classified as a clockwise (CW) alignment.

In some embodiments, phase contrast imaging is used to determine directionality of the cell. In some embodiments, phase contrast imaging of the cell is used to determine directionality. In some embodiments, phase contrast imaging of at least a portion of the substrate micropattern is used to determine directionality. In some embodiments, phase contrast imaging of the cell and at least a portion of the substrate micropattern is used to determine directionality.

In some embodiments, cell migration is actin-associated. In some embodiments, cell migration is not tubulin-associated. In some embodiments, cell migration is not mysosin-associated. In some embodiments, cell migration is not tubulin-associated or mysosin-associated.

Another aspect is a method for diagnosing a disease or disorder. In some embodiments, the method includes determining chirality of a cell, as described above; comparing the chirality of that cell with the chirality known to be associated with that cell type; and correlating a change in the chirality of the cell compared to that of its cell type with a disease or disorder. In some embodiments, a change in the chirality of the cell compared to that of its cell type is correlated with cancer. In some embodiments, a change in the chirality of the cell compared to that of its cell type is correlated with exposure to a teratogen. In some embodiments, a change in the chirality of the cell compared to that of its cell type is correlated with a genetic disease. In some embodiments, a change in the chirality of the cell opposite that of its cell type is correlated with a disease or disorder.

Another aspect provides a method of screening an agent for effects on cell chirality. In some embodiments, the method includes contacting a candidate agent and a cell of a first cell type; determining chirality of the cell, as described above; and selecting an agent that produces a change in the chirality of the cell compared to the first cell type.

Other objects and features will be in part apparent and in part pointed out hereinafter.

DESCRIPTION OF THE DRAWINGS

Those of skill in the art will understand that the drawings, described below, are for illustrative purposes only. The drawings are not intended to limit the scope of the present teachings in any way.

(FIG. 2A) Asymmetric cell alignment on ring patterns (phase contrast image). (FIG. 2B) Cell alignment directions (green lines). (FIG. 2C) The biased angle of cell alignment (green lines) was defined as either CW or CCW, based on the deviation from the circumferential direction (blue dash line). (FIG. 2D) The circular histogram of biased angles shows CCW chirality. (FIG. 2E) Circumferential averages of the sub-regional biased angles at different radial positions on the ring (mean±s.e.m.). (FIG. 2F) The histogram of the mean biased angles of C2C12 cells (33 experiments, >1000 ring patterns).

(FIG. 3A-F). Cells on strip and ring geometries clearly demonstrate asymmetric alignment, while those residing on the circular and square patterns do not. (FIG. 3G). A schematic of the conformity in the biased cell alignment between cells on strips and cells on rings. Green lines indicate the direction of cell alignment, while blue and red lines represent the opposite boundaries of strips or rings. Ring geometry shows a consistent biased alignment regardless of whether the linear strip was bent upward or downward to create ring geometry, suggesting that the left-right asymmetry is independent of the ring curvature. Scale bars: 100 µm.

(FIG. 4A) Cells on a ring "sense" the z-axis through attachment to the substrate and the x axis through the ring boundaries. The cell alignment bias of the y-axis (dash red lines) creates the observed cellular chiral behavior or LR asymmetry. (FIG. 4B) Centrosomes (bright green) are positioned closer to each boundary than nuclei (blue) in C2C12 cells (actin: red, tubulin: green). (FIG. 4C) Golgi apparatus (red) is positioned closer to ring boundaries than nuclei (blue) in hUVEC cells. (FIG. 4D) Average velocity and direction of C2C12 cells are indicated by arrow direction and length, respectively. (FIG. 4E) Average velocity of C2C12 cell migration in the circumferential ($V_\theta$) and the radial direction ($V_r$) as a function of radial position. (FIG. 4F) Average velocity and (FIG. 4G) the circumferential migration velocity of hUVEC cells at the inner and outer ring boundary as a function of time.

(FIG. 6A) Phase contrast images and (FIG. 6B) chirality of C2C12 cells on micro-patterned rings in the presence of Latrunculin A, Cytochalasin D, Jasplakinolide, Nocodazole, and Taxol. Scale bars: 100 µm. (FIG. 6C) Latrunculin A does not change the polarity of C2C12 cells, as the cells positioned their centrosome (bright green), rather than the nucleus (blue), closer to ring boundaries. Scale bars: 50 µm. (FIG. 6D) Migration of C2C12 cells in the presence of Latrunculin A, with the direction and magnitude of velocity indicated by arrow direction and length, respectively. (FIG. 6E) Average velocity of the cells along the circumferential direction ($V_\theta$) and the radial direction ($V_r$) as a function of radial position.

(FIG. 7A). Phase contrast images of the cells (top) at 5, 10, 20, and 30 hours after cell seeding and the corresponding histograms (bottom) of biased angles from the sub-regions for each image. Scale bars: 100 µm. (FIG. 7B). The time history of the mean biased angle of C2C12 cells on a ring, with the insert for cell number increasing exponentially with time.

DETAILED DESCRIPTION OF THE INVENTION

Figure 1:
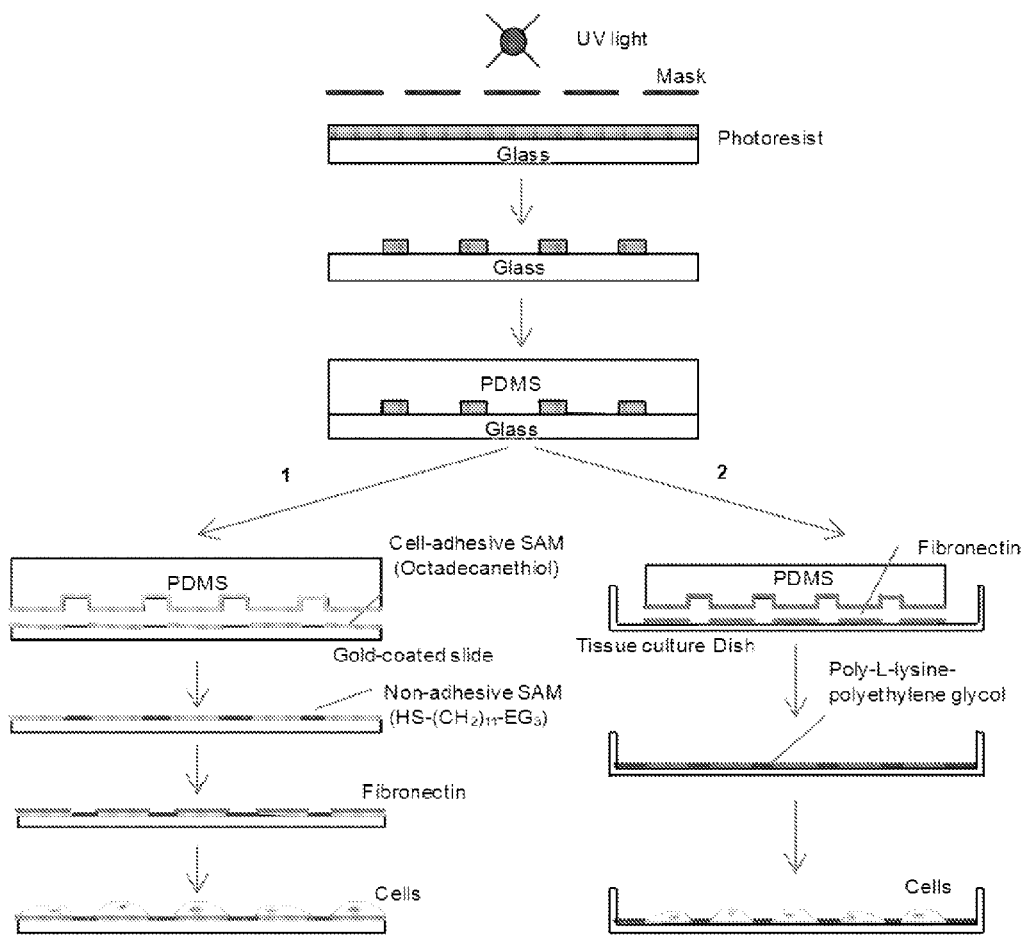
FIG. 1 is cartoon showing micro-fabrication and micro-contact printing for cell patterning. A negative photoresist mold was made first by UV (ultraviolet) crosslinking through a mask containing desired micropatterning features. PDMS (polydimethylsiloxane) elastomeric stamps were then casted with prepolymers onto the mold. In most experiments (path 1), octadecanethiol, an adhesive self-assembly monolayer (SAM), was transferred via the PDMS stamp onto gold-coated glass slides, which were then sequentially subjected to a non-adhesive ethylene glycol-terminated SAM HS-$(CH_2)_{11}$-$EG_3$ and fibronectin. Alternatively (path 2), fibronectin was stamped onto tissue culture treated plastic, which was subsequently backfilled with poly-L-lysine-polyethylene glycol and washed with PBS for cell seeding.

The present application is based at least in part on the surprising discovery that directional cell movement on a micro-patterned substrate was not random but, rather, significantly biased towards either left or right orientation (chirality) in a way that was specific to the cell phenotype. In brief, cells cultured on micropatterns with defined appositional boundaries exhibit chiral morphogenesis that can be readily determined by analysis of cell alignment and directional motion. In studies of various cell types on several thousand patterns, it was observed that cell chirality was defined by cell phenotype, and that loss of actin but not microtubule function could reverse the CCW cell chirality. Experiments presented herein demonstrate that normal and cancer cells of the same type can have opposite chirality; certain drugs that promote cancer can reverse cell chirality of healthy control cells; the chirality of normal human cells can be reverted by exposure to mutagens; actin inhibitors can reverse cell chirality; and cancer cell chirality depends on actin function.

Shown herein are experiments with micro-patterned substrates having geometrically defined features, such as rings or linear strips, with a width of about 50 to about 200 pm. The cell density in experiments described herein was in the range of about 20,000 to about 50,000 cells cm$^{-2}$, which was dependent on cell size. The chiral alignment and biased migration of the cells on boundaries of micro-patterns was determined by light microscopy and quantified by automated imaging processing. Chiral cell alignment was determined from phase contrast images taken after about 12 to about 24 hours of culture. Cell migration analysis was from videos taken between about 5 to about 30 hours, at 5 minutes per frame. Directional motion of cultured cells was observed for specific pattern geometries (shape and size), which can be due to the effects of alignment and boundaries, factors that are important in early development. The micro-patterns were shown to induce cell elongation along the circumferential direction of the ring or the length direction on the linear strip, and cell polarization on boundaries. Cells were shown to migrate within such patterns taking either left or right direction (i.e., clockwise or counterclockwise on ring patterns). It was also shown that cell chirality related to actin function. Significant chirality according to cell phenotype was demonstrated with p values in the range of $10^{-7}$ to $10^{-185}$. Furthermore, cancer cells were shown to possess a chirality opposite of that for corresponding non-cancer cells.

Provided herein is a micro-assay to determine cellular chirality (left right asymmetry). In various embodiments, a simple and highly accurate in vitro platform described herein can be used to study the initiation of chiral morphogenesis and identify genetic, biochemical and environmental factors leading to malformations.

Substrate and Micropattern

As described herein, a substrate having a micropattern can be provided. The substrate can be of any material suitable for cell growth (see e.g., Freshney 2010 Culture of Animal Cells: A Manual of Basic Technique and Specialized Applications, 6th Ed., Wiley-Blackwell, ISBN-10: 9780470528129; Helgason and Miller 2004 Basic Cell Culture Protocols, 3d Ed., Humana Press, ISBN-10: 1588292843). A substrate can be, for example, a coated slide (see e.g., Wan et al. 2010 Integr Biol (Camb) 2, 346-353. An exemplary substrate is a gold-coated glass (e.g., about 100 Å to about 200 Å gold thickness)

A substrate can be a coated substrate. A substrate can be coated with, for example, an attachment protein. Exemplary attachment proteins include fibronectin.

As described herein, a micropattern can be provided on a substrate. The micropattern can be of the same or similar material as the substrate or a different material from the substrate.

A substrate can include a micropattern of a variety of geometric configurations. For example, a substrate can include a ring micropattern. As another example, a substrate can include a linear micropattern. As another example, a substrate can include a semi-linear micropattern.

A micropattern can be formed on a substrate according to, for example, micro-contact printing to pattern shaped monolayers stamped on the substrate. A micropattern can be formed on a substrate via polydimethylsiloxane (PDMS) elastomeric stamps and self-assembly monolayers (SAMs) (see e.g., Example 1).

A micropatterned substrate can be formed from a master mold fabricated with a suitable photoresist material (e.g., SU-8 2050 photoresist, MicroChem Corp, Newton, Mass.) and a suitable mask (e.g., chromium mask) with desired geometric features. A polymeric composition (e.g., PDMS pre-polymer and curing agent, Dow Corning, Midland, Mich.) can be introduced into or onto the mold and cured.

A self assembling monolayer (e.g., an adhesive SAM octadecanethiol, Sigma) can be transferred onto the substrate (e.g., gold-coated (150 Å in thickness) with the PDMS stamp. The substrate can be coated with an additional self assembling monolayer (e.g., a non-adhesive ethylene glycol-terminated SAM, $HS-(CH_2)_{11}-EG_3$, Prochimia, Poland). A patterned substrate can be washed with a suitable solvent (e.g., ethanol). A patterned substrate can be coated with a substance to facilitate cell attachment (e.g., fibronectin).

A PDMS stamp can be coated with a substance to facilitate cell attachment (e.g., fibronectin) and placed onto a suitable substrate (e.g., tissue culture-treated dish). A coated PDMS stamp on a suitable substrate can be coated with a suitable self assembling monolayer (e.g., non-adhesion SAM, 100 µg/ml poly-L-lysine-polyethylene glycol, PLL-g-PEG; Susos AG, Dübendorf, Switzerland). A stamped substrate can be washed with a suitable solution, such as phosphate buffered saline (PBS).

A micropatterned substrate can include a path for cells to be cultured on. The path can be the portion of a micropatterned substrate on which a cell can orient or migrate. For example, a cultured cell can migrate along the path of the micropatterned substrate.

A micropatterned substrate can include one or more boundaries. The shape or contour of a boundary can depend on the geometry of the micropatterned substrate. A boundary of a micropatterned substrate can be adjacent to the path. A boundary can function to impede or stop migration or orientation of a cell cultured on a micropatterned substrate. For example, a cultured cell can migrate along the path of the micropatterned substrate until encountering a boundary.

A micropattern boundary can be an inner boundary or an outer boundary. The inner boundary and the outer boundary can have the same or different shapes depending on the geometry of the micropatterned substrate. For example, for a micropatterned substrate including a ring shaped pattern, the inner boundary and the outer boundary can each mimic or substantially mimic the shape of the ring but each with a different radius. As another example, for a micropatterned substrate including a linear strip shaped pattern, the inner boundary and the outer boundary can be parallel or substantially parallel.

Figure 4:
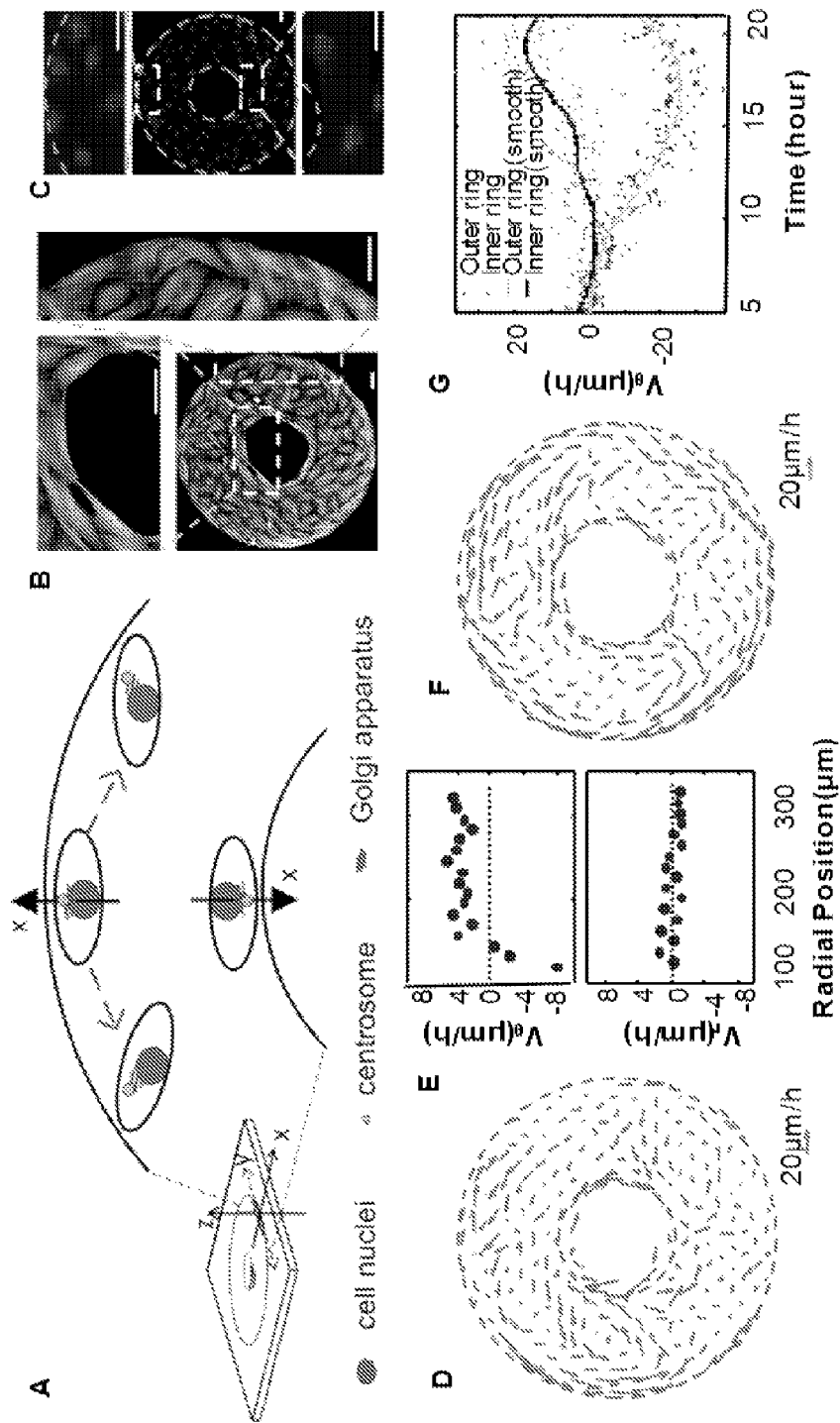
FIG. 4 is a series of a schematic diagrams, phase contrast images, and a line and scatter plot showing chirality on micropatterned rings is established by mechanisms involving boundary effects. Scale bars: 50 µm.

A substrate having a micropattern can be oriented around multiple axes. For example, a micropatterned substrate can have an x-axis, a y-axis, and a z-axis (see e.g., FIG. 4).

The x-axis of a micropatterned substrate can be oriented across the path. The x-axis of a micropatterned substrate can be substantially perpendicular to the path. As an example, where a micropatterned substrate has a ring shape, the x-axis of a micropatterned substrate can be oriented or substantially oriented according to the radius of curvature of the ring shape. As another example, where a micropatterned substrate has a linear shape, the x-axis of a micropatterned substrate can be perpendicular or substantially perpendicular to one or more boundaries.

The y-axis of a micropatterned substrate can be oriented with or substantially with the path. For example, where a micropatterned substrate has a ring shape, the x-axis of a micropatterned substrate can be oriented or substantially oriented according to the circumferential direction of the path (see e.g., FIG. 4

The inner boundary and outer boundary can be separated by a distance so as to form a path or a portion of the path. The path, or a portion thereof, can be defined by the inner boundary, the outer boundary, or the inner boundary and the outer boundary. In some embodiments, the inner boundary and the outer boundary can be separated by about 100 µm to about 300 µm. For example, the inner boundary and the outer boundary can be separated by about 100 µm, about 150 µm, about 200 µm, about 250 µm, or about 300 µm. The distance between the inner boundary and the outer boundary can be as measured anywhere along the path. The distance between the inner boundary and the outer boundary can be as measured along the x-axis.

A micropatterned substrate in the shape of a ring can have an inner diameter of at least about 150 µm. For example, a micropatterned substrate in the shape of a ring can have an inner diameter of at least about 200 µm, at least about 250 µm, at least about 300 µm, or at least about 350 µm.

Cell

As described herein, a cell can be cultured on a micropatterned substrate so as to determine chirality.

A cell can be any cell of interest. A cell can be any cell for which determination of chirality is desired. A cell can be an animal cell. A cell can be a mammalian cell. A cell can be derived from an animal, including, but not limited to, mammals, reptiles, and avians, more preferably horses, cows, dogs, cats, sheep, pigs, and chickens, and most preferably human. A cell can be, for example, an exocrine secretory epithelial cell, a hormone secreting cell, an epithelial cell lining a closed internal body cavity, a keratinizing epithelial cell, a wet stratified barrier epithelial cell, a sensory transducer cell, an autonomic neuron cell, a sense organ and peripheral neuron supporting cell, a central nervous system neuron, a central nervous system glial cells, a lens cell, a metabolism and storage cell, a barrier function cell (e.g., lung, gut, exocrine glands or urogenital tract), a kidney cell, an extracellular matrix cell, a contractile cell, a blood and immune system cell, a pigment cell, a germ cell, a nurse cell, or an interstitial cell. For example, a cell can be an endothelial cell, a fibroblast cell, a stem cell (e.g., a mesenchymal stem cell), a skeletal muscle cell, an osteoblast cell, or a myoblast cell.

A cell can be isolated, purified, or cultured by a variety of means known to the art Methods for the isolation and culture of cells are discussed in, for example, Vunjak-Novakovic and Freshney (2006) Culture of Cells for Tissue Engineering, Wiley-Liss, ISBN 0471629359.

A cell can be a wild type cell or a transgenic cell. Compositions and methods described herein utilizing molecular biology protocols can be according to a variety of standard techniques known to the art (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754; Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

A cell cultured on a micropatterned substrate can undergo orientation, re-orientation, or migration. Orientation, re-orientation, or migration of a cell on a micropatterned substrate can be indicative of chirality of the cell, as described herein.

Orientation, re-orientation, or migration of a cell proximal to a micropattern boundary on a micropatterned substrate can be indicative of chirality of the cell, as described herein.

Orientation, re-orientation, or migration of a cell in contact with a micropattern boundary on a micropatterned substrate can be indicative of chirality of the cell, as described herein.

Cells can be cultured on micropatterned substrate at any density suitable for determination of orientation or direction of migration, as described herein. Cell density can be optimized according to factors including, but not limited to, cell type, substrate type, micropattern type, micropattern shape, or culture conditions. In some embodiments, cells can be cultured on a micropatterned substrate at a density of about 2,000 cells $cm^{-2}$ to about 500,000 cells $cm^{-2}$. For example, cells can be cultured on a micropatterned substrate at a density of about 20,000 cells $cm^{-2}$ to about 50,000 cells $cm^{-2}$. For example, cells can be cultured on a micropatterned substrate at a density of about 2,000 cells $cm^{-2}$; about 5,000 cells $cm^{-2}$; about 10,000 cells $cm^{-2}$; about 15,000 cells $cm^{-2}$; about 20,000 cells $cm^{-2}$; about 25,000 cells $cm^{-2}$; about 30,000 cells $cm^{-2}$; about 35,000 cells $cm^{-2}$; about 40,000 cells $cm^{-2}$; about 45,000 cells $cm^{-2}$; about 50,000 cells $cm^{-2}$; about 100,000 cells $cm^{-2}$; about 150,000 cells $cm^{-2}$; about 200,000 cells $cm^{-2}$; about 250,000 cells $cm^{-2}$; about 300,000 cells $cm^{-2}$; about 350,000 cells $cm^{-2}$; about 400,000 cells $cm^{-2}$; about 450,000 cells $cm^{-2}$; or about 500,000 cells $cm^{-2}$.

Chirality

As described herein, chirality can be determined for a cell cultured on a micropatterned substrate. Chirality can be a leftward directionality of migration of a cell. Chirality of a cell can be a leftward directional alignment of a cell. Chirality can be a rightward directionality of migration of a cell. Chirality of a cell can be a rightward directional alignment of a cell.

Determination of chirality can occur when a cell is proximal to one or more micropattern boundaries of a micropatterned substrate. Determination of chirality can occur when a cell is in contact with one or more micropattern boundaries of a micropatterned substrate.

Directionality of cell alignment or motion can be according to measurement of a pattern of angular deviation from a reference. Directionality can be measured along the y-axis. For example, directionality can be measured as an angular deviation of alignment or migration of the cell from the y-axis. As another example, directionality can be measured as a departure of migration direction along the y-axis. As another example, directionality can be measured as the angle of orientation of the cell with respect to the y-axis.

For example, directionality can be measured as angular deviation of alignment or migration of the cell away from the y-axis, where a positive angular deviation greater than about 1 degree can be classified as a counterclockwise (CCW) alignment. As another example, directionality can be measured as angular deviation of alignment or migration of the cell away from the y-axis, where a positive angular deviation greater than about 2 degrees, greater than about 3 degrees, greater than about 4 degrees, greater than about 5 degrees, greater than about 6 degrees, greater than about 7 degrees, greater than about 8 degrees, greater than about 9 degrees, greater than about 10 degrees, greater than about 11 degrees, greater than about 12 degrees, greater than about 13 degrees, greater than about 14 degrees or greater than about 15 degrees is classified as a counterclockwise (CCW) alignment.

For example, directionality can be measured as angular deviation of alignment or migration of the cell away from the y-axis, where a negative angular deviation less than about negative 1 degree can be classified as a clockwise (CW) alignment. As another example, directionality can be measured as angular deviation of alignment or migration of the cell away from the y-axis, where a negative angular deviation less than about negative 2 degrees, less than about negative 3 degrees, less than about negative 4 degrees, less than about negative 5 degrees, less than about negative 6 degrees, less than about negative 7 degrees, less than about negative 8 degrees, less than about negative 9 degrees, less than about negative 10 degrees, less than about negative 11 degrees, less than about negative 12 degrees, less than about negative 13 degrees, less than about negative 14 degrees or less than about negative 15 degrees is classified as a clockwise (CW) alignment.

Directionality can be measured with respect to the x axis. Determination of directionality can employ a reference of the x-axis from one point to a second point so as to establish a point of reference for leftward or rightward.

A point to point reference along the x-axis can be according to features of the micropatterned substrate. For example, directionality can be measured with respect to the path to the inner boundary along the x-axis. As another example, directionality can be measured with respect to the path to the outer boundary along the x-axis.

A point to point reference along the x-axis can be according to features of the cell for which chirality is to be determined. For example, directionality can be measured with respect to the x-axis from a nucleus of the cell to a centrosome of the cell along the x-axis. As another example, directionality can be measured with respect to the nucleus of the cell to a Golgi apparatus of the cell along the x-axis.

Determination of chirality can be according to analysis of an image of a cell on the micropatterned substrate. The image can be, for example, a phase contrast image. Analysis to determine chirality of a cell on a micropatterned substrate can be a manual analysis. Analysis to determine chirality of a cell on a micropatterned substrate can be an automated analysis (see e.g., Example 7). Programs for determining cell alignment (see e.g., Karlon et al. 1999 Ann Biomed Eng 27, 712-720) can be modified so as to determine cell chirality (see e.g., Example 7). An automated analysis to determine cell chirality (e.g., from phase contrast images of patterned surfaces) can reduce or substantially eliminate bias in chirality determination as well as increase throughput.

Any of the above methods to determine chirality of a cell can be applied to a population of cells. Determination of chirality of a type of cell can be according to a mean directionality of a plurality of cells.

Algorithm

Another aspect of the present disclosure is directed to an algorithm for determining cell chirality. Such algorithm can be used to determine cell chirality from, for example, phase contrast images of patterned surfaces. Such algorithm can avoid bias in chirality determination.

The following describes an image-processing algorithm to determine cellular chirality (left right asymmetry, handedness) on micro-patterned surfaces towards potential applications in disease detection and drug screening. The algorithm can be used with, for example, methods for cell, printing, cultivation and the acquisition of phase contrast images described herein. A program implementing such algorithm can provide automated determination of the chirality of patterned cells.

An algorithm to determine cellular chirality from, for example, phase contrast images of cells cultured on micropatterned surfaces with defined boundaries can be as follows. The description below is based on a radial micropatterned surfaces. One of ordinary skill will understand such techniques can be applied to other micropattern shapes discussed herein.

Images of cell patterns can be examined and those failing to form a near perfect, a substantially perfect, or a perfect shape according to the defined boundaries (e.g., a ring) can be excluded from further analysis. For each image, the center of the ring can be determined using an interactive script (e.g., a MatLab interactive script). The direction of cell alignment in subregions can be determined based on increased brightness of the contour of a cell contour in phase contrast images as compared to the interior region of the cell. An intensity gradient can be determined (e.g., pixel by pixel) with a filter (e.g., a Gaussian differential filter). In each sub-region of the image, the dominant local direction can be determined using an accumulator scheme, for example, one in which the orientation of each pixel follows a von Mises distribution, a circular analogue of the linear normal distribution. The biased angle of the cell axis can then be calculated for each subregion based on the deviation of cell alignment direction from the circumferential direction. The cell alignment can then be determined for an individual ring with an appropriate statistical test (e.g., a Rayleigh test, which is an analog to the Student t-test in a linear system). Cell chirality can be determined as the directionality of cell motion, and can be designated as clockwise or counterclockwise, using, for example, tens or hundreds of rings tested as described above.

The above steps can be performed automatically (e.g., according to a MatLab program). A program encoding the above described algorithm can be extended to determine cell chirality on patterned long strips (e.g., lines).

Correlation to Disease

A determination of chirality can be correlated to a disease or disorder. For example, a change in chirality from that normally associated with a particular cell type can indicate a disease or disorder. Such correlation can provide a protocol for diagnosing or confirming a diagnosis of a disease or disorder.

A change in chirality can be, for example, an opposite chirality from that normally associated with a particular cell type. A change in chirality can be, for example, an exaggerated or amplified chirality from that normally associated with a particular cell type.

For example, a determination of a change in chirality from that normally associated with a particular cell type can indicate the tested cell is a cancerous cell. For example, a determination of a change in chirality as compared to the chirality normally associated with a particular cell type can indicate the tested cell is a cancerous cell. As shown herein, mouse and human skeletal muscle cells (hSkMCs) showed a CCW alignment, while other tested cell types exhibited a CW alignment (see e.g., Table 1; Example 3). Furthermore, cancer skin cells also exhibited a CCW alignment (see e.g., Table 1; Example 3).

Cancer types generally include carcinoma (malignant tumors derived from epithelial cells, including breast, prostate, lung and colon cancer); sarcoma (malignant tumors derived from connective tissue, or mesenchymal cells); lymphoma and leukemia (malignancies derived from hematopoietic cells); germ cell tumor (tumors derived from totipotent cells); cancer stem cells, blastic tumor or blastoma (tumor resembling an immature or embryonic tissue). Cancers include, but are not limited to, gastrointestinal tumors, cancer of liver and biliary tract, pancreatic cancer, prostatic cancer, testicular cancer, colorectal cancer, lung cancer, breast cancer, cutaneous melanoma, ovarian cancer, uterine cancer, cervical cancer, endometrial cancer, cancer of the head and neck, brain, bladder cancer, leukemia, non-Hodgkin lymphoma, sarcomas and osteosarcomas, Kaposi sarcoma, AIDS-related Kaposi sarcoma, and renal carcinoma. A cell type, as used herein, can be any cell associated with a cancer described above. A determination of a change in chirality from that normally associated with a particular cell type can indicate the tested cell is a cancerous cell of a type described above.

Birth defects can be associated with genetic diseases or prenatal exposure to teratogens, which impact cell chirality. A determination of a change in chirality as compared to the chirality normally associated with a particular cell type can indicate the tested cell has been exposed to a teratogen. A determination of a change in chirality as compared to the chirality normally associated with a particular cell type can indicate the tested cell has a genetic abnormality associated with a genetic disease or disorder in a subject.

Mechanism

While under no obligation to do so, and in no way limiting the scope of the present disclosure, the inventors provide the following mechanistic description.

Two competing mechanisms may co-exist within cells to determine their LR decisions or chirality. One mechanism would require actin function and lead to the intrinsic "leftward" bias at the boundaries and subsequent CCW alignment in chiral morphogenesis. The second mechanism would induce intrinsic "rightward" bias at the boundaries and a CW alignment in chiral morphogenesis. The differences in chirality may be due to the higher expression of actin in muscle cells than other cells (N. Shimizu, T. Obinata, J Biochem 99, 751 (March, 1986); I. M. Herman, Curr Opin Cell Biol 5, 48 (February, 1993)), necessitating identification of cell-type-related determinants of chirality in tissue development. Actin bundles were reported to account for cardiac looping, the first visible sign of LR asymmetry in vertebrate embryos (L. A. Taber, Int J Dev Biol 50, 323 (2006); N. Itasaki, H. Nakamura, H. Sumida, M. Yasuda, Anat Embryol (Berl) 183, 29 (1991)).

While the exact mechanism detailing how actin affects cell chirality is still unknown, drug treatment data presented herein (see Example 6) shows that mammalian muscle cells share similarities in their chirality with invertebrate cells, such as those in snail embryos (Y. Shibazaki, M. Shimizu, R. Kuroda, Curr Biol 14, 1462 (Aug. 24, 2004)). It is thought that mediation of actin expression levels in the establishment and reversal of cell chirality may be through the non-canonical Wnt signaling pathway, which plays a critical role in pattern determination during embryonic development (C. Pohl, Z. Bao, Dev Cell 19, 402 (Sep. 14, 2010)).

Screening

Determination of chirality of a cell cultured on a micropatterned substrate can be used in screening protocols. For example, methods described herein can be used for screening effects of candidate agents on a cells chirality.

The subject methods find use in the screening of a variety of different candidate molecules (e.g., potentially therapeutic candidate molecules). Candidate substances for screening according to the methods described herein include, but are not limited to, fractions of tissues or cells, nucleic acids, polypeptides, siRNAs, antisense molecules, aptamers, ribozymes, triple helix compounds, antibodies, and small (e.g., less than about 2000 mw, or less than about 1000 mw, or less than about 800 mw) organic molecules or inorganic molecules including but not limited to salts or metals.

Candidate molecules encompass numerous chemical classes, for example, organic molecules, such as small organic compounds having a molecular weight of more than 50 and less than about 2,500 Daltons. Candidate molecules can comprise functional groups necessary for structural interaction with proteins, particularly hydrogen bonding, and typically include at least an amine, carbonyl, hydroxyl or carboxyl group, and usually at least two of the functional chemical groups. The candidate molecules can comprise cyclical carbon or heterocyclic structures and/or aromatic or polyaromatic structures substituted with one or more of the above functional groups.

A candidate molecule can be a compound in a library database of compounds. One of skill in the art will be generally familiar with, for example, numerous databases for commercially available compounds for screening (see e.g., ZINC database, UCSF, with 2.7 million compounds over 12 distinct subsets of molecules; Irwin and Shoichet (2005) J Chem Inf Model 45, 177-182). One of skill in the art will also be familiar with a variety of search engines to identify commercial sources or desirable compounds and classes of compounds for further testing (see e.g., ZINC database; eMolecules.com; and electronic libraries of commercial compounds provided by vendors, for example: ChemBridge, Princeton BioMolecular, Ambinter SARL, Enamine, ASDI, Life Chemicals etc).

Candidate molecules for screening according to the methods described herein include both lead-like compounds and drug-like compounds. A lead-like compound is generally understood to have a relatively smaller scaffold-like structure (e.g., molecular weight of about 150 to about 350 kD) with relatively fewer features (e.g., less than about 3 hydrogen donors and/or less than about 6 hydrogen acceptors; hydrophobicity character x log P of about −2 to about 4) (see e.g., Angewante (1999) Chemie Int. ed. Engl. 24, 3943-3948). In contrast, a drug-like compound is generally understood to have a relatively larger scaffold (e.g., molecular weight of about 150 to about 500 kD) with relatively more numerous features (e.g., less than about 10 hydrogen acceptors and/or less than about 8 rotatable bonds; hydrophobicity character x log P of less than about 5) (see e.g., Lipinski (2000) J. Pharm. Tox. Methods 44, 235-249). Preferably, initial screening is performed with lead-like compounds.

When designing a lead from spatial orientation data, it can be useful to understand that certain molecular structures are characterized as being "drug-like". Such characterization can be based on a set of empirically recognized qualities derived by comparing similarities across the breadth of known drugs within the pharmacopoeia. While it is not required for drugs to meet all, or even any, of these characterizations, it is far more likely for a drug candidate to meet with clinical successful if it is drug-like.

Several of these "drug-like" characteristics have been summarized into the four rules of Lipinski (generally known as the "rules of fives" because of the prevalence of the number 5 among them). While these rules generally relate to oral absorption and are used to predict bioavailability of compound during lead optimization, they can serve as effective guidelines for constructing a lead molecule during rational drug design efforts such as may be accomplished by using the methods of the present disclosure.

The four "rules of five" state that a candidate drug-like compound should have at least three of the following characteristics: (i) a weight less than 500 Daltons; (ii) a log of P less than 5; (iii) no more than 5 hydrogen bond donors (expressed as the sum of OH and NH groups); and (iv) no more than 10 hydrogen bond acceptors (the sum of N and O atoms). Also, drug-like molecules typically have a span (breadth) of between about 8 Å to about 15 Å.

Kits

Also provided are kits. Such kits can include a micropatterned substrate or components for production thereof, and, in certain embodiments, instructions for administration. Such kits can facilitate performance of the methods described herein. When supplied as a kit, the different components of the composition can be packaged in separate containers and admixed immediately before use. Components include, but are not limited to micropatterned substrates, cell culture reagents, or analytical software. Such packaging of the components separately can, if desired, be presented in a pack or dispenser device which may contain one or more components. The pack may, for example, comprise metal or plastic foil such as a blister pack. Such packaging of the components separately can also, in certain instances, permit long-term storage without losing activity of the components.

Kits may also include reagents in separate containers such as, for example, sterile water or saline to be added to a lyophilized active component packaged separately. For example, sealed glass ampules may contain a lyophilized component and in a separate ampule, sterile water, sterile saline or sterile each of which has been packaged under a neutral non-reacting gas, such as nitrogen. Ampules may consist of any suitable material, such as glass, organic polymers, such as polycarbonate, polystyrene, ceramic, metal or any other material typically employed to hold reagents. Other examples of suitable containers include bottles that may be fabricated from similar substances as ampules, and envelopes that may consist of foil-lined interiors, such as aluminum or an alloy. Other containers include test tubes, vials, flasks, bottles, syringes, and the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like.

In certain embodiments, kits can be supplied with instructional materials. Instructions may be printed on paper or other substrate, and/or may be supplied as an electronic-readable medium, such as a floppy disc, mini-CD-ROM, CD-ROM, DVD-ROM, Zip disc, videotape, audio tape, and the like. Detailed instructions may not be physically associated with the kit; instead, a user may be directed to an Internet web site specified by the manufacturer or distributor of the kit.

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise.

In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1

Microcontact Printing

Cell patterning was done by using polydimethylsiloxane (PDMS) elastomeric stamps and self-assembly monolayers (SAMs) (L. Q. Wan et al., Integr Biol (Camb) 2, 346 (Aug.

10, 2010); C. S. Chen, M. Mrksich, S. Huang, G. M. Whitesides, D. E. Ingber, Science 276, 1425 (May 30, 1997); M. Thery, M. Piel, Cold Spring Harb Protoc 2009, pdb prot5255 (July, 2009)). A master mold was first fabricated with SU-8 2050 photoresist (MicroChem Corp, Newton, Mass.) and chromium masks with desired geometric features. The mixture (10:1) of PDMS pre-polymer and curing agent (Dow Corning, Midland, Mich.) was poured into the mold and cured at 70° C. for 4 hours.

An adhesive SAM octadecanethiol (Sigma) was transferred onto the gold-coated (150 Å in thickness) glass slide with the PDMS stamp (see e.g., FIG. 1) (L. Q. Wan et al., Integr Biol (Camb) 2, 346 (Aug. 10, 2010)). The slide was then immersed in a non-adhesive ethylene glycol-terminated SAM (HS-$(CH_2)_{11}$-$EG_3$, Prochimia, Poland) for 3 hours. Finally, patterned surfaces were washed with ethanol and coated with 10 μg/ml fibronectin (Sigma) for 30 minutes.

Alternatively (see e.g., FIG. 1), the PDMS stamp was coated with 50 μg/ml fibronectin for 30 minutes, aspirated, and dried in the air for 1 minute (M. Thery, M. Piel, Cold Spring Harb Protoc 2009, pdb prot5255 (July, 2009)). The stamp was then gently placed onto tissue culture-treated dishes for 2 minutes, and incubated in a non-adhesion SAM, 100 μg/ml poly-L-lysine-polyethylene glycol (PLL-g-PEG; Susos AG, Dübendorf, Switzerland), for 1 hour. Finally the surface was washed with phosphate buffered saline (PBS).

Cell Culture.

Cells were maintained in tissue flasks with culture media specified in TABLE 2. After reaching 70% confluency, cells were trypsinized and seeded onto protein-coated patterned surfaces. Once the cells attached, extra cells were washed off with fresh medium. At this time drugs were added into the culture medium if necessary. Phase contrast images were taken after overnight incubation at 37° C. and 5% $CO_2$ when cells reached confluency on the ring patterns.

Drug Treatment.

To examine the role of actin in left-right (LR) asymmetry, cells were tested with 20-500 nM Latrunculin A, 0.05-1.0 μg/ml Cytochalasin D, and 1-100 nM Jasplakinolide. Latrunculin A inhibits actin polymerization by forming a 1:1 molar complex with G-actin, thereby inhibiting its ability to polymerize into F-actin (M. Coue, S. L. Brenner, I. Spector, E. D. Korn, FEBS Lett 213, 316 (Mar. 23, 1987)). Cytochalasin D inhibits actin polymerization by binding to the growing ends of F-actin chains and thus preventing the attachment and addition of G-actin monomers (J. A. Cooper, J Cell Biol 105, 1473 (October, 1987)). Jasplakinolide is known to bind to and stabilize actin filaments in vitro (M. R. Bubb, I. Spector, B. B. Beyer, K. M. Fosen, J Biol Chem 275, 5163 (Feb. 18, 2000)).

To examine the role of microtubules in LR asymmetry, 0.2-2 μM Nocodazole, and 0.3-30 nM Taxol were used. Nocodazole suppresses microtubule dynamics by destabilizing and disassembling microtubules (J. A. Cooper, J Cell Biol 105, 1473 (October, 1987)). Taxol inhibits the microtubule depolymerization and stabilizes microtubules (W. B. Derry, L. Wilson, M. A. Jordan, Biochemistry 34, 2203 (Feb. 21, 1995)).

To examine the role of the actomyosin motor, cells were tested with 0.2-10 mM Y-27632, 1-20 mM ML-7, and 0.5-10 mM Blebbistatin. Y-27632 works as a selective inhibitor to prevent the phosphorylation of the myosin regulatory light chain (T. Ishizaki et al., Mol Pharmacol 57, 976 (May, 2000)). ML-7 acts as a selective inhibitor of the myosin light chain kinase (M. Isemura, T. Mita, K. Satoh, K. Narumi, M. Motomiya, Cell Biol Int Rep 15, 965 (October, 1991)). Blebbistatin forms a low actin affinity complex through binding to myosin heads, causing the inhibition of non-muscle myosin II ATPase activity (M. Kovacs, J. Toth, C.

TABLE 2

Compositions of cell culture media. DMEM: Dulbecco's Modified Eagle Medium; P/S: penicillin/streptomycin; and FBS: fetal bovine serum; C2C12: mouse skeletal muscle C2C12 cell line; hUVEC: human umbilical vein endothelial cells; NIH/3T3: mouse embryonic fibroblast cell line; hASC: human adipose-derived stem cells; hMSC: human bone marrow-derived mesenchymal stem cells; hSkMC: human skeletal muscle cell line; MC-3T3: mouse osteoblast cell line.

| Cell Type | Base Medium Source | Composition |
|---|---|---|
| C2C12 | Invitrogen Cat# 21068 | DMEM with 10% FBS, 1% P/S, 1 mM sodium pyruvate |
| hUVEC | Lonza Cat# CC-3156 Cat# CC-4176 | Endothelial Basal Medium-2 (EBM-2) supplemented with EGM-2 SingleQuot Kit supplement & growth factors |
| NIH/3T3 | Invitrogen Cat# 21068 | DMEM with 10% FBS, 1% P/S, 1 mM sodium pyruvate |
| hASC | Invitrogen Cat# 21068 | DMEM with 10% FBS, 1% P/S, 1 mM sodium pyruvate |
| hMSC | Invitrogen Cat# 21068 | DMEM with 10% FBS, 1% P/S, 1 mM sodium pyruvate |
| hSkMC | Lonza Cat# CC-3161 Cat# CC-3160 | SkMC Basal Media supplemented with SkMC SingleQuot Kit supplement & growth factors |
| MC-3T3 | Invitrogen Cat# 12561 | Minimum essential α Medium with 10% fetal bovine serum, 1% penicillin/streptomycin |
| Human primary skin fibroblast | Invitrogen Cat# 21068 | DMEM with 10% FBS, 1% P/S, 1 mM sodium pyruvate |
| Human skin fibroblast line | Invitrogen Cat# 21068 | DMEM with 10% FBS, 1% P/S, 1 mM sodium pyruvate |
| Rat cardiac fibroblast | Invitrogen Cat# 21068 | DMEM with 10% FBS, 1% P/S, 1 mM sodium pyruvate penicillin/streptomycin, 1 mM sodium pyruvate |

Hetenyi, A. Malnasi-Csizmadia, J. R. Sellers, J Biol Chem 279, 35557 (Aug. 20, 2004)).

Immunofluorescence Staining.

After imaging, cells were fixed with 4% formaldehyde in cytoskeletal buffer (10 mM MES, 138 mM KCl, 3 mM $MgCl_2$, 2 mM EGTA, and 0.32 M sucrose) for 25 minutes. For actin/tubulin double staining, the cells were incubated with phalloidin-TRITC (1:400; Invitrogen) and anti-Tubulin-FITC (1:50; Sigma) for 1 hour. For the Golgi apparatus positioning inside patterned rings, the cells were incubated in 1 μg/ml anti-human golgin-97 (Invitrogen) for 1 hour. After secondary antibodies, cell nuclei were stained with 200 ng/ml 40, 6-diamidino-2-phenylindole (DAPI; Sigma) for 10 minutes. Finally, the cells were mounted with Fluoromount-G medium (SouthernBiotech, Birmingham, Ala.).

Analysis of Cell Alignment.

High-resolution phase contrast images of live patterned cells were taken at a resolution of ~0.645 μm/pixel, and analyzed using a custom-written code in MatLab (MathWorks, Natick, Mass.), based on the automated detection of intensity gradient and circular statistics (W. J. Karlon et al., Ann Biomed Eng 27, 712 (November-December, 1999)). In this algorithm, the intensity gradient was determined pixel by pixel with a Gaussian differential filter. In each sub-region of the image, the dominant local direction was determined using an accumulator scheme, in which the orientation of each pixel follows a von Mises distribution, a circular analogue of the linear normal distribution. Subsequently, the orientation in each sub-region was converted into an angle bias based on its deviation from the circumferential direction (see e.g., FIG. 2C). Mean angle and standard deviation of LR asymmetry were calculated for all sub-regions, using circular statistics (N. I. Fish, Statistical Analysis of Circular Data. (Cambridge University Press, Cambridge, UK, 1993)). It was verified that the variation of sub-region size from 10 by 10 pixels to 60 by 60 pixels would not significantly alter the judgment of cell chirality on rings. The sub-region size was therefore set to 20 by 20 pixels (i.e., 13 by 13 μm).

Analysis of Cell Migration.

For time-lapse videos, cells were patterned on a gold-coated glass-bottom Petri dish (ibid, München, Germany). After cells attached, the dish was transferred into an environmental chamber (37° C. and 5% $CO_2$) and image time series were recorded every 5 minutes at a resolution of 1.56 μm/pixel for a total time of 20-40 hours. As the image capture rate is much higher than the characteristic time for cell migration, digital image correlation, together with sub-pixel displacement estimation, were used to determine the displacements of cell migration. A FFT (fast Fourier transform)-based method was first utilized to match regions of two sequential phase contrast images. The calculated displacement values were then used as inputs for a more accurate estimation of displacement fields at a sub-pixel level, using a second-order image correlation algorithm described previously (P. Zhou, K. E. Goodson, Opt Eng 40, 1613 (August, 2001)). To evaluate the bias of cell migration, the obtained velocity field was further projected in the circumferential ($V_θ$) and radial ($V_r$) direction.

Statistical Analysis.

Cell chirality on ring patterns (i.e., clockwise or counter-clockwise alignment) was determined from calculated biased angles in local regions with one sample test for the mean angle, analogous to the one sample t-test in linear statistics (N. I. Fish, Statistical Analysis of Circular Data. (Cambridge University Press, Cambridge, UK, 1993)). The overall biased behavior of the cells was tested based on the number of rings exhibiting either clockwise or counter clockwise alignment in the rank test, with confidence level set to 0.05.

Example 2

It was thought by the inventors that populations of cells of the same type, if cultured within patterns with well-defined boundaries, would express directional alignment and motion associated with the establishment of chiral morphogenesis. Methods are according to Example 1, unless otherwise specified.

Figure 3:
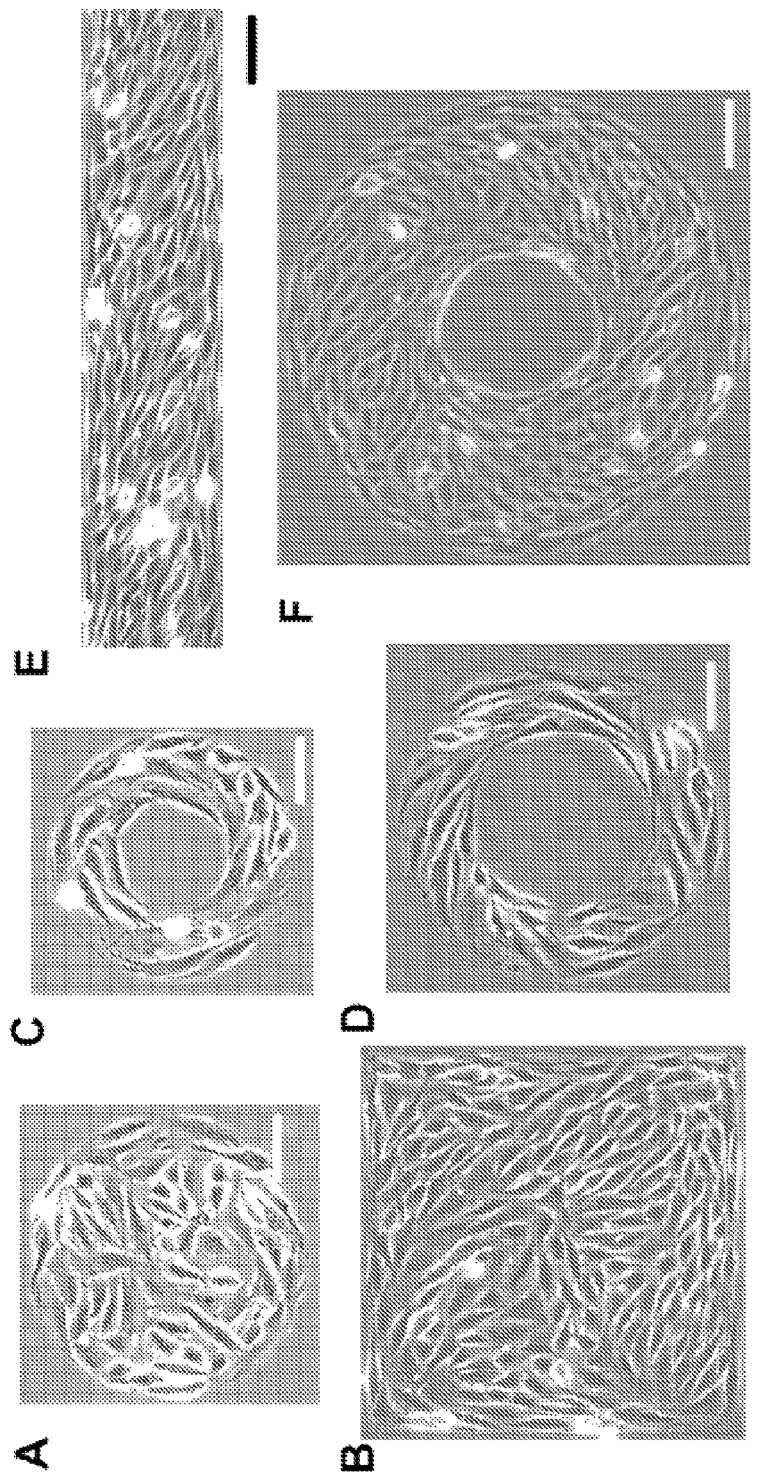
FIG. 3 is a series of phase contrast images and a schematic diagram showing C2C12 cells grown on micro-patterned surfaces.
Figure 3:
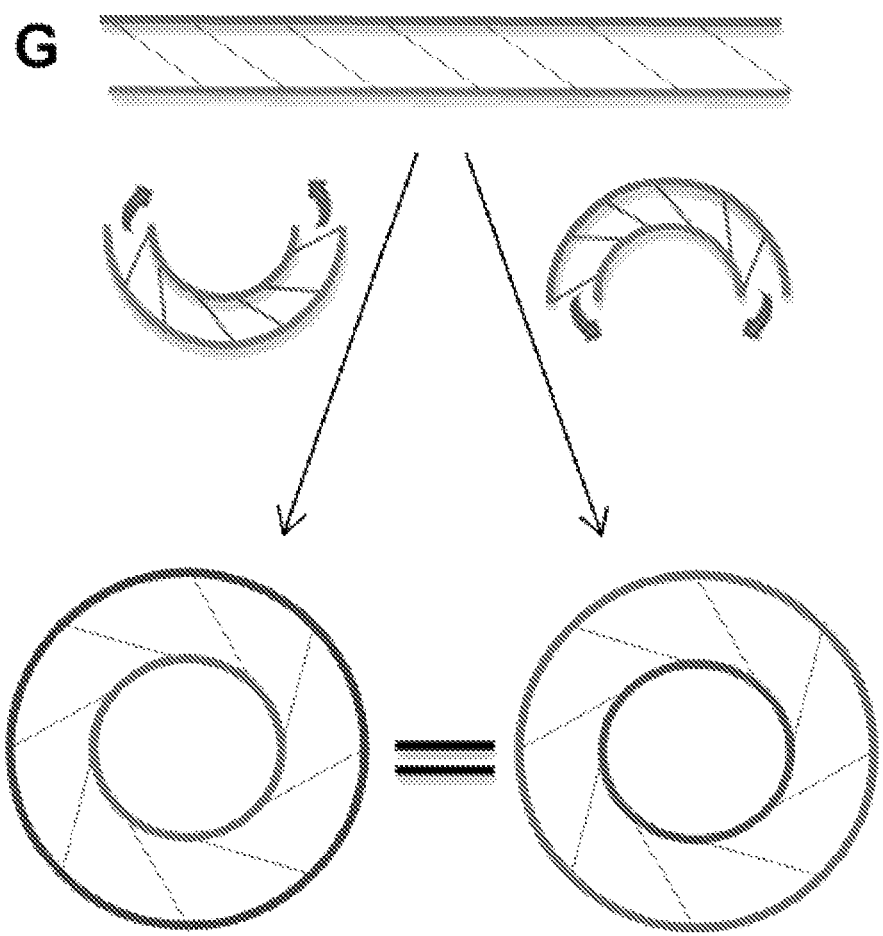

C2C12 murine myoblasts were cultured on micropatterns with well-defined boundaries, such as circles, squares, linear strips, and rings (see e.g., FIG. 1) (L. Q. Wan et al., Integr Biol (Camb) 2, 346 (Aug. 10, 2010); C. S. Chen, M. Mrksich, S. Huang, G. M. Whitesides, D. E. Ingber, Science 276, 1425 (May 30, 1997)). Biased cell alignment was observed on linear strips and rings but not on circles and squares (see e.g., FIG. 3 A-F), suggesting the importance of appositional boundaries for the expression of chirality. Because equivalent bias in cell alignment was observed on linear strips and rings of different sizes (see e.g., FIG. 3 G), rings with an inner diameter of 250 μm and a distance of 200 μm between the inner and outer boundary were used in subsequent studies.

Figure 2:
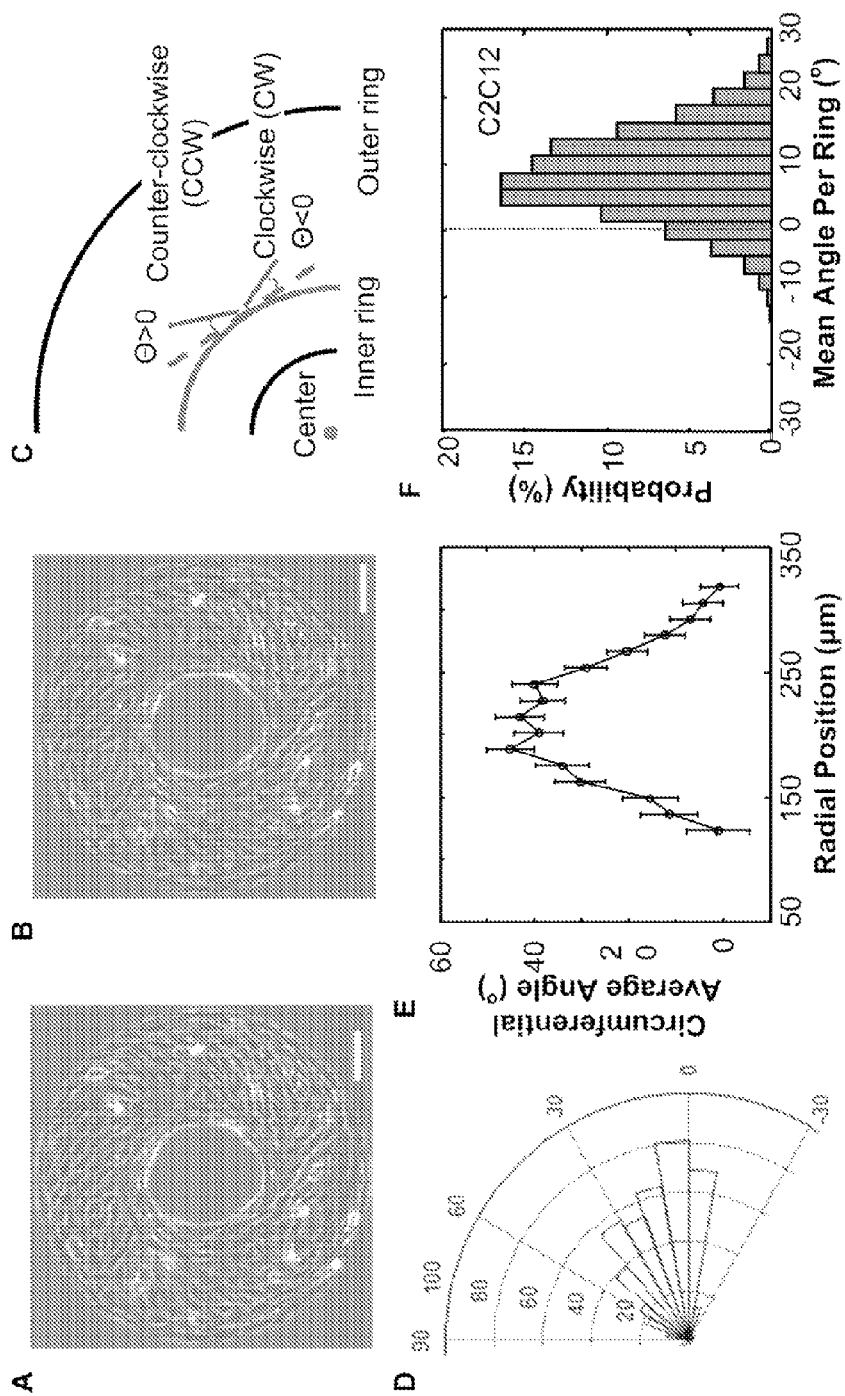
FIG. 2 is a series of phase contrast images, schematic diagrams, line and mean plot, and a bar graph showing mouse myoblasts (C2C12) exhibiting distinct chirality on micropatterned surfaces. Scale bars: 100 µm.

Phase contrast images, in which cell contour appears brighter than the inner cell region, were used to measure cell alignment (W. J. Karlon et al., Ann Biomed Eng 27, 712 (November-December, 1999)) (see e.g., FIG. 2A), as indicated by green lines in FIG. 2B. Each green line was assigned a biased angle between −90° and 90°, based on its deviation from the circumferential direction (blue dash line); a positive value represented a counter clockwise (CCW) alignment, while a negative value represented a clockwise (CW) alignment (FIG. 2C). An angular histogram (FIG. 2D) and the radial distribution (FIG. 2E) of the measured angles revealed preference for positive angles, corresponding to the CCW bias. In >30 independent series of experiments using >1000 individual rings (FIG. 2F), the C2C12 cells showed CCW alignment with a biased angle of 8.47°±0.20° (mean±s.e.m.), with very strong statistical significance ($p=9.3 \times 10^{-186}$).

Example 3

The following example shows determination of chirality for various cell types. Methods are according to Examples 1-2, unless specified otherwise.

Figure 5:
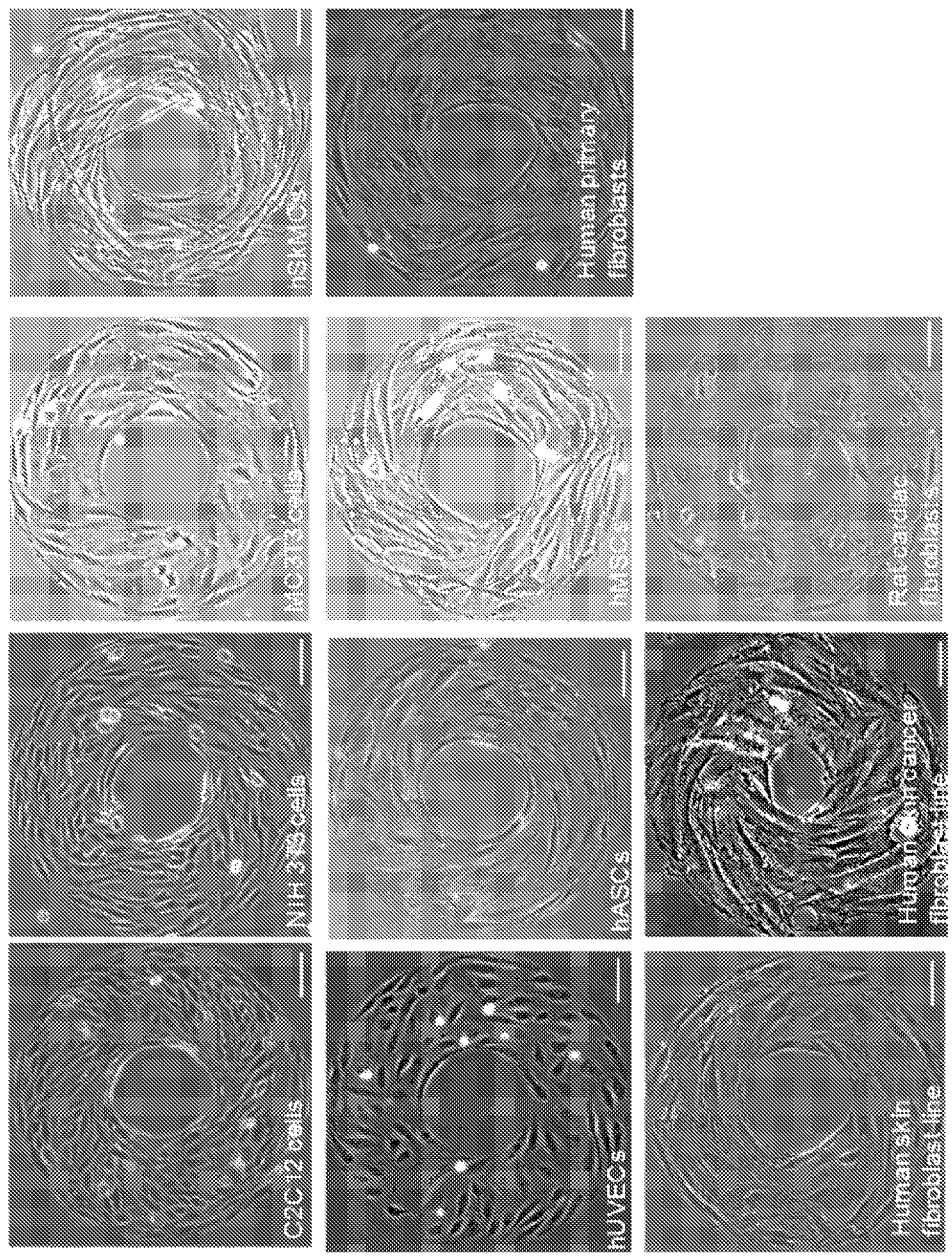
FIG. 5 is a series of phase contrast images of various cell types. The C2C12 cells and human skeletal muscle cells exhibit a counter-clockwise alignment while other cells that were studied show a clockwise alignment. The human skin cancer fibroblast cell line show a counter-clockwise alignment, opposite from healthy human skin fibroblasts. Scale bars: 100 µm.

A panel of mouse, rat, and human cells (Table 1, FIG. 5) derived from skeletal muscle, bone, adipose tissue, skin, heart, and blood vessels were tested for chirality.

Results showed that mouse (C2C12) and human skeletal muscle cells (hSkMCs) showed a CCW alignment, while all other cell types exhibited a CW alignment (see e.g., TABLE 1, TABLE 3, TABLE 4). Cancer skin cells also exhibited a CCW alignment. These data suggest that adherent mammalian cells exhibit an invariant chirality determined by the cell phenotype and disease condition.

TABLE 1

Cell chirality on patterned substrates depends on cell phenotype and disease condition.

| Cell Description | Num of Exps | CW | N/S | CCW | p Value | Species | Tissue | Phenotype | Cell Culture | Catalog Number |
|---|---|---|---|---|---|---|---|---|---|---|
| C2C12 | 33 | 34 | 172 | 850 | $9.3 \times 10^{-186}$ | mouse | skeletal muscle | myoblast | cell line | ATCC CRL-1772 |
| NIH/3T3 | 4 | 51 | 20 | 8 | $4.5 \times 10^{-9}$ | mouse | embryo | fibroblast | cell line | ATCC CRL-1658 |
| MC3T3-E1 | 3 | 65 | 70 | 19 | $2.4 \times 10^{-7}$ | mouse | calvaria | osteoblast | cell line | ATCC CRL-2593 |
| rat cardiac fibroblast | 7 | 100 | 66 | 17 | $8.6 \times 10^{-16}$ | rat | heart | cardiac fibroblast | primary cells | — |
| hUVEC | 11 | 307 | 65 | 16 | $5.0 \times 10^{-61}$ | human | umbilical vein | endothelial cells | primary cells | — |
| hSkMC | 5 | 16 | 67 | 80 | $1.0 \times 10^{-11}$ | human | skeletal muscle | myoblast | cell line | Lonza CC-2661 |
| hASC | 3 | 44 | 21 | 3 | $1.2 \times 10^{-10}$ | human | adipose | stem cells | primary cells | — |
| hMSC | 2 | 42 | 7 | 7 | $1.5 \times 10^{-7}$ | human | bone marrow | stem cells | primary cells | — |
| human primary skin fibroblast | 6 | 172 | 24 | 2 | $6.1 \times 10^{-42}$ | human | skin | fibroblast | primary cells | ATCC PCS-201-012 |
| human skin fibroblast line | 4 | 49 | 31 | 19 | $1.8 \times 10^{-4}$ | human | skin | fibroblast | cell line | ATCC CRL-7761 |
| human skin cancer fibroblast line | 3 | 32 | 49 | 58 | 0.004 | human | skin | fibroblast | cell line | ATCC CRL-7762 |

"—" indicates that cells were isolated in the lab; CW: clockwise alignment; CCW: counter-clockwise alignment; N/S: not significantly biased to CW or CCW.

TABLE 3

The chirality of mouse myoblast cell line C2C12 on ring patterns. CW: clockwise alignment, CCW: counter-clockwise alignment, and N/S: not significantly biased to CW or CCW.

| C2C12 | CW | N/S | CCW | Biased? | p Value |
|---|---|---|---|---|---|
| 1 | 0 | 1 | 21 | Y | $4.8 \times 10^{-7}$ |
| 2 | 0 | 2 | 37 | Y | $7.3 \times 10^{-12}$ |
| 3 | 2 | 7 | 29 | Y | $2.3 \times 10^{-7}$ |
| 4 | 0 | 4 | 18 | Y | $3.8 \times 10^{-6}$ |
| 5 | 0 | 1 | 25 | Y | $3.0 \times 10^{-8}$ |
| 6 | 0 | 1 | 28 | Y | $3.7 \times 10^{-9}$ |
| 7 | 0 | 3 | 19 | Y | $1.9 \times 10^{-6}$ |
| 8 | 0 | 2 | 25 | Y | $3.0 \times 10^{-8}$ |
| 9 | 0 | 0 | 28 | Y | $3.7 \times 10^{-9}$ |
| 10 | 0 | 0 | 45 | Y | $2.8 \times 10^{-14}$ |
| 11 | 0 | 2 | 27 | Y | $7.5 \times 10^{-9}$ |
| 12 | 0 | 4 | 31 | Y | $4.7 \times 10^{-10}$ |
| 13 | 6 | 29 | 29 | Y | $5.8 \times 10^{-5}$ |
| 14 | 4 | 27 | 8 | N | 0.19 |
| 15 | 3 | 7 | 21 | Y | $1.4 \times 10^{-4}$ |
| 16 | 0 | 2 | 10 | Y | $9.8 \times 10^{-4}$ |
| 17 | 0 | 0 | 21 | Y | $4.8 \times 10^{-7}$ |
| 18 | 0 | 6 | 29 | Y | $1.9 \times 10^{-9}$ |
| 19 | 3 | 4 | 19 | Y | $4.3 \times 10^{-4}$ |
| 20 | 0 | 7 | 7 | Y | $7.8 \times 10^{-3}$ |
| 21 | 2 | 7 | 37 | Y | $1.4 \times 10^{-9}$ |
| 22 | 4 | 8 | 11 | Y | 0.04 |
| 23 | 1 | 4 | 27 | Y | $1.0 \times 10^{-7}$ |
| 24 | 1 | 6 | 35 | Y | $5.2 \times 10^{-10}$ |
| 25 | 0 | 3 | 28 | Y | $3.7 \times 10^{-9}$ |
| 26 | 1 | 3 | 28 | Y | $5.4 \times 10^{-8}$ |
| 27 | 0 | 4 | 36 | Y | $1.5 \times 10^{-11}$ |
| 28 | 1 | 5 | 42 | Y | $4.9 \times 10^{-12}$ |
| 29 | 2 | 7 | 21 | Y | $3.0 \times 10^{-5}$ |
| 30 | 1 | 6 | 27 | Y | $1.0 \times 10^{-7}$ |
| 31 | 3 | 8 | 36 | Y | $1.7 \times 10^{-8}$ |
| 32 | 0 | 1 | 21 | Y | $4.7 \times 10^{-7}$ |
| 33 | 0 | 1 | 24 | Y | $6.0 \times 10^{-8}$ |
| Sum | 34 | 172 | 850 | Y | $1.6 \times 10^{-254}$ |

TABLE 4

The chirality of human umbilical vein endothelial cells, hUVECs on ring patterns. CW: clockwise alignment, CCW: counter-clockwise alignment, and N/S: not significantly biased to CW or CCW.

| hUVEC | CW | N/S | CCW | Biased? | p Value |
|---|---|---|---|---|---|
| 1 | 17 | 0 | 0 | Y | $7.6 \times 10^{-6}$ |
| 3 | 13 | 7 | 4 | Y | 0.018 |
| 4 | 22 | 2 | 1 | Y | $2.7 \times 10^{-6}$ |
| 5 | 31 | 6 | 1 | Y | $7.5 \times 10^{-9}$ |
| 6 | 10 | 1 | 0 | Y | $9.8 \times 10^{-4}$ |
| 7 | 25 | 14 | 2 | Y | $2.6 \times 10^{-6}$ |
| 8 | 15 | 4 | 1 | Y | $2.4 \times 10^{-4}$ |
| 9 | 35 | 8 | 2 | Y | $4.8 \times 10^{-9}$ |
| 10 | 26 | 6 | 1 | Y | $2.0 \times 10^{-7}$ |
| 11 | 26 | 4 | 0 | Y | $1.5 \times 10^{-8}$ |
| 12 | 24 | 4 | 1 | Y | $7.5 \times 10^{-7}$ |
| 13 | 34 | 7 | 1 | Y | $1.0 \times 10^{-9}$ |
| 14 | 29 | 2 | 2 | Y | $2.2 \times 10^{-7}$ |
| Sum | 307 | 65 | 16 | Y | $2.7 \times 10^{-71}$ |

For cells on a patterned geometry to display their chirality and to distinguish between left and right (y-axis), the polarity of the z-axis (up-down) and x-axis (front-back) must be established (see e.g., FIG. 4A). Notably, the z-axis was established independent of gravity direction, as observed experimentally in vertically inverted cell cultures (TABLE 5).

TABLE 5

Effects of culture conditions on cell chirality. The cells retained their chirality under inverted culture (upside down) as compared to that at normal condition, suggesting that there is no effect of gravity.

| Culture  | CW | N/S | CCW | p Value              |
|----------|----|-----|-----|----------------------|
| Normal   | 2  | 7   | 21  | $3.3 \times 10^{-5}$ |
| Inverted | 1  | 7   | 26  | $2.1 \times 10^{-7}$ |

The geometric boundaries determined organelle positioning (i.e., x-axis), with centrosomes (bright green, see e.g., FIG. 4B) and Golgi apparatus (red, see e.g., FIG. 4C) being positioned closer to the boundaries than the cell nucleus (blue) (R. A. Desai, L. Gao, S. Raghavan, W. F. Liu, C. S. Chen, *J Cell Sci* 122, 905 (Apr. 1, 2009)), independent of the gravitational direction. In addition, cell chirality was maintained on patterns with different surface chemistry, and after the disruption of cadherin function (see e.g., FIG. 1, TABLE 6, TABLE 7).

TABLE 6

Effects of culture conditions on cell chirality. Cell chirality did not alter with protein coating with fibronectin, Type I collagen, laminin and Matrigel. CW: clockwise alignment, CCW: counter-clockwise alignment, and N/S: not significantly biased to CW or CCW.

| Substrate Protein | CW | N/S | CCW | p Value               |
|-------------------|----|-----|-----|-----------------------|
| Fibronectin       | 1  | 4   | 32  | $2.0 \times 10^{-9}$  |
| Collagen I        | 0  | 0   | 23  | $1.2 \times 10^{-7}$  |
| Laminin           | 2  | 2   | 34  | $9.2 \times 10^{-9}$  |
| Matrigel          | 0  | 5   | 35  | $2.9 \times 10^{-11}$ |

TABLE 7

Effects of culture conditions on cell chirality. Cell chirality was also conserved at reduced cell-cell interactions under low calcium conditions (either following the addition of a calcium chelator, EGTA, or in calcium-free culture medium). CW: clockwise alignment, CCW: counter-clockwise alignment, and N/S: not significantly biased to CW or CCW.

| Culture          | CW | N/S | CCW | p Value              |
|------------------|----|-----|-----|----------------------|
| Control          | 1  | 3   | 28  | $5.6 \times 10^{-8}$ |
| 0.5 mM EGTA      | 0  | 2   | 24  | $3.0 \times 10^{-8}$ |
| 2 mM EGTA        | 1  | 3   | 12  | $1.7 \times 10^{-3}$ |
| $Ca^{2+}$ free medium | 1 | 3 | 26  | $2.1 \times 10^{-7}$ |

Example 4

For further insight into the biased cell alignment, C2C12 cell motion was analyzed. Methods are according to Examples 1-3, unless specified otherwise.

Figure 7:
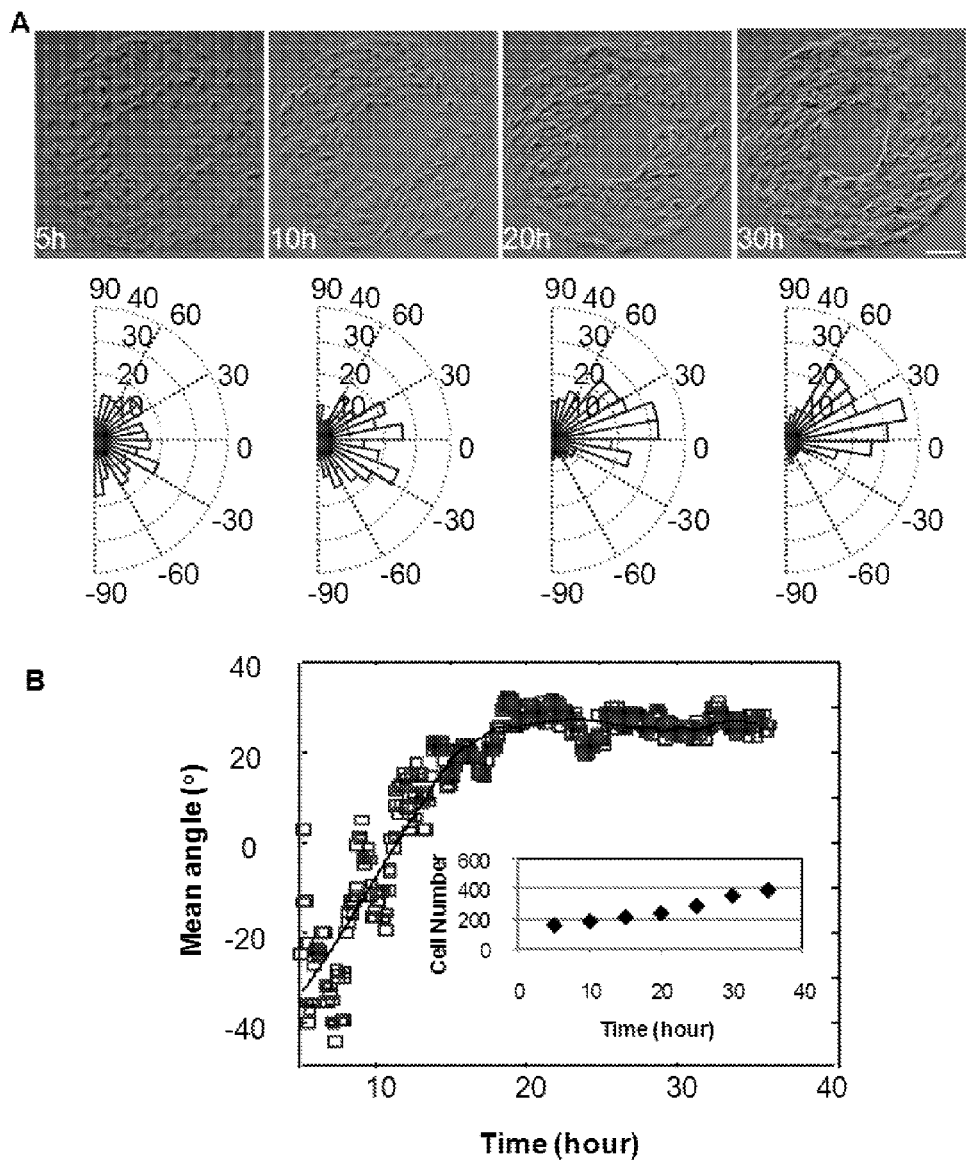
FIG. 7 is a series of phase contrast images and a line and scatter plot showing cellular alignment of patterned C2C12 cells over time.

Cell alignment did not show a clear bias before confluency (FIG. 7), suggesting that the inhibition of random walk through physical contact was necessary for the cells to exhibit chirality. The cells were labeled and tracked along the inner and outer ring pattern, and the cell migration velocity was estimated by digital image correlation (P. Zhou, K. E. Goodson, Opt Eng 40, 1613 (August, 2001)). The speed of migration was higher at the inner and outer ring boundaries (~25 μm/hr in average) than within the interior region (~10 μm/hr). The average velocity (see e.g., FIG. 4D) and the velocity changes in radial and circumferential directions (see e.g., FIG. 4E) demonstrated that the cells migrated in the CW direction at the inner ring boundary (at 8 μm/hr), and in the CCW direction at the outer ring boundary (at 4 μm/hr).

At the level of an individual cell, this seemingly opposite circular motion of cells on the inner and outer boundary is in fact consistent with biased migration. Based on cell polarization at boundaries, the x-axis can be defined as the direction from the nucleus to centrosome (J. Xu et al., Proc Natl Acad Sci USA 104, 9296 (May 29, 2007)), as shown in, for example, FIG. 4A. Cell migration can thus be considered as "leftward bias" along both the inner and outer ring boundary. Also, cell alignment on micropatterns is related to the cell migration at the boundaries, as seen for a C2C12 cell migrating towards a boundary and adopting the leftward biased migration. Because cell polarization and biased migration occur at the boundaries of micropatterns, cell proximity to a boundary is necessary for the expression of chirality. This finding was further supported by the biased cell alignment being most clearly seen in the regions close to the boundaries, especially for less elongated cells such as cardiac fibroblasts (see e.g., FIG. 5).

Example 5

The following example shows mean biased angle of human umbilical cord endothelial cells (hUVEC). Methods are according to Examples 1-4, unless specified otherwise.

The mean biased angle of hUVEC on rings was similar in magnitude to that of C2C12 cells, but was negative (−8.47°+/−0.33°, n=388), indicating a CW alignment. By the time the cell chirality was established (15-20 hours after seeding), cells along the boundaries had a significantly higher migration speed (35 μm/hr) than those in the interior regions (20 μm/hr). In contrast to C2C12 cells, hUVEC migration was in the CCW direction at the inner ring boundary (15 μm/hr) and in the CW direction at the outer ring boundary (20 μm/hr) (see e.g., FIG. 4G). Based on the x-axis directed from the nucleus to the centrosome/Golgi apparatus, the migration of hUVECs exhibited a "rightward" bias.

Example 6

Figure 6:
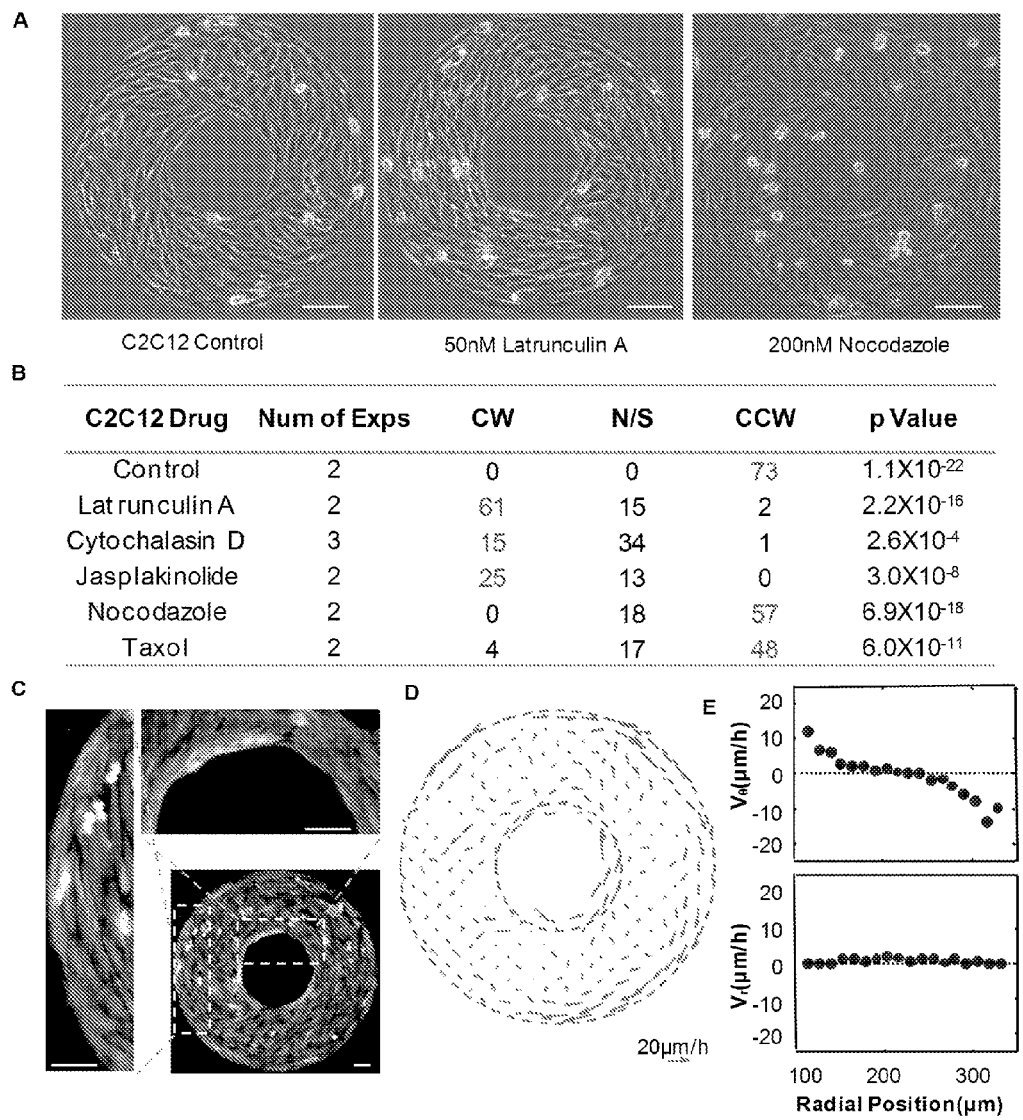
FIG. 6 is a series of phase contrast images, a table, a schematic diagram, and a scatter plot showing chirality of muscle cells requires functional actin but not tubulin.

To investigate the roles of actin and tubulin, cyoskeletal proteins putatively linked to cell chirality (W. Edwards, A. T. Moles, P. Franks, Global Ecol Biogeogr 16, 795 (November, 2007); Y. Shibazaki, M. Shimizu, R. Kuroda, Curr Biol 14, 1462 (Aug. 24, 2004); P. Spéder, G. Adam, S. Noselli, Nature 440, 803 (Apr. 6, 2006); S. Hozumi et al., Nature 440, 798 (Apr. 6, 2006); J. Xu et al., Proc Natl Acad Sci USA 104, 9296 (May 29, 2007)), the dynamics of their polymerization and depolymerization were inhibited (see e.g., FIG. 6A-B). Methods are according to Examples 1-5, unless specified otherwise.

For C2C12 and hUVEC cells, cell alignment on micropatterned rings followed a dose-dependent response (TABLE 8).

TABLE 8

Effects of actin and tubulin blockers. Dose-dependent changes in the left-right asymmetry of cells on patterned surfaces to various drugs that interfere with the actin and microtubule function. CW: clockwise alignment, CCW: counter-clockwise alignment, and N/S: not significantly biased to CW or CCW.

| Cell type | Drug | Concentration | CW | N/S | CCW | p Value |
|---|---|---|---|---|---|---|
| C2C12 | Latrunculin A | 0 nM | 0 | 0 | 73 | $1.1 \times 10^{-22}$ |
|  |  | 50 nM | 61 | 15 | 2 | $2.1 \times 10^{-16}$ |
|  |  | 200 nM | 57 | 7 | 0 | $6.9 \times 10^{-18}$ |
|  |  | 500 nM | 1 | 10 | 0 | 0.5 |
|  | Cytochalasin D | 0 µg/mL | 1 | 6 | 35 | $5.2 \times 10^{-10}$ |
|  |  | 0.05 µg/mL | 9 | 6 | 8 | 0.19 |
|  |  | 0.1 µg/mL | 7 | 10 | 3 | 0.12 |
|  |  | 0.2 µg/mL | 21 | 23 | 5 | $9.8 \times 10^{-4}$ |
|  |  | 0.5 µg/mL | 10 | 14 | 0 | $9.8 \times 10^{-4}$ |
|  |  | 1 µg/mL | 8 | 20 | 1 | 0.018 |
|  | Jasplakinolide | 0 nM | 1 | 6 | 27 | $1.0 \times 10^{-7}$ |
|  |  | 1 nM | 2 | 10 | 34 | $9.2 \times 10^{-9}$ |
|  |  | 3 nM | 3 | 4 | 18 | $6.3 \times 10^{-4}$ |
|  |  | 10 nM | 7 | 5 | 14 | 0.055 |
|  |  | 30 nM | 18 | 4 | 0 | $3.8 \times 10^{-6}$ |
|  |  | 100 nM | 7 | 9 | 0 | $7.8 \times 10^{-3}$ |
|  | Nocodazole | 0 nM | 0 | 0 | 73 | $1.1 \times 10^{-22}$ |
|  |  | 200 nM | 0 | 18 | 57 | $6.9 \times 10^{-18}$ |
|  |  | 500 nM | 0 | 58 | 35 | $2.9 \times 10^{-11}$ |
|  |  | 1 µM | 0 | 21 | 18 | $3.8 \times 10^{-6}$ |
|  |  | 2 µM | 0 | 6 | 1 | 0.5 |
|  | Taxol | 0 nM | 3 | 8 | 36 | $1.7 \times 10^{-8}$ |
|  |  | 0.3 nM | 1 | 3 | 24 | $7.5 \times 10^{-7}$ |
|  |  | 1 nM | 1 | 6 | 20 | $1.0 \times 10^{-5}$ |
|  |  | 3 nM | 2 | 9 | 31 | $6.1 \times 10^{-8}$ |
|  |  | 10 nM | 2 | 8 | 17 | $3.3 \times 10^{-4}$ |
|  |  | 30 nM | 2 | 13 | 16 | $5.8 \times 10^{-4}$ |
| hUVEC | Latrunculin A | 0 nM | 38 | 21 | 6 | $4.0 \times 10^{-7}$ |
|  |  | 20 nM | 36 | 8 | 0 | $1.4 \times 10^{-11}$ |
|  |  | 50 nM | 2 | 19 | 0 | 0.25 |
|  |  | 200 nM | 2 | 56 | 5 | 0.16 |
|  |  | 500 nM | 2 | 42 | 1 | 0.38 |
|  | Cytochalasin D | 0 | 26 | 6 | 1 | $2.0 \times 10^{-7}$ |
|  |  | 0.1 µg/mL | 8 | 12 | 0 | $3.9 \times 10^{-3}$ |
|  |  | 0.2 µg/mL | 10 | 22 | 0 | $9.8 \times 10^{-4}$ |
|  |  | 0.5 µg/mL | 0 | 6 | 1 | 0.5 |
|  | Jasplakinolide | 0 nM | 34 | 7 | 1 | $1.0 \times 10^{-9}$ |
|  |  | 1 nM | 32 | 1 | 1 | $3.8 \times 10^{-9}$ |
|  |  | 3 nM | 22 | 5 | 2 | $1.6 \times 10^{-5}$ |
|  |  | 10 nM | 22 | 10 | 5 | $6.0 \times 10^{-4}$ |
|  |  | 30 nM | 5 | 4 | 0 | 0.031 |
|  |  | 100 nM | 1 | 5 | 0 | 0.5 |
|  | Nocodazole | 0 nM | 28 | 21 | 6 | $4.0 \times 10^{-7}$ |
|  |  | 200 nM | 25 | 76 | 3 | $1.2 \times 10^{-5}$ |
|  |  | 500 nM | 14 | 27 | 2 | $1.8 \times 10^{-3}$ |
|  |  | 1 µm | 3 | 4 | 0 | 0.125 |
|  |  | 2 µm | 1 | 7 | 0 | 0.5 |
|  | Taxol | 0 nM | 29 | 2 | 2 | $2.2 \times 10^{-7}$ |
|  |  | 0.3 nM | 8 | 0 | 0 | $3.9 \times 10^{-3}$ |
|  |  | 1 nM | 34 | 4 | 1 | $1.0 \times 10^{-9}$ |
|  |  | 3 nM | 7 | 9 | 2 | 0.07 |
|  |  | 10 nM | 10 | 11 | 5 | 0.09 |
|  |  | 30 nM | 4 | 7 | 2 | 0.23 |

Figure 8:
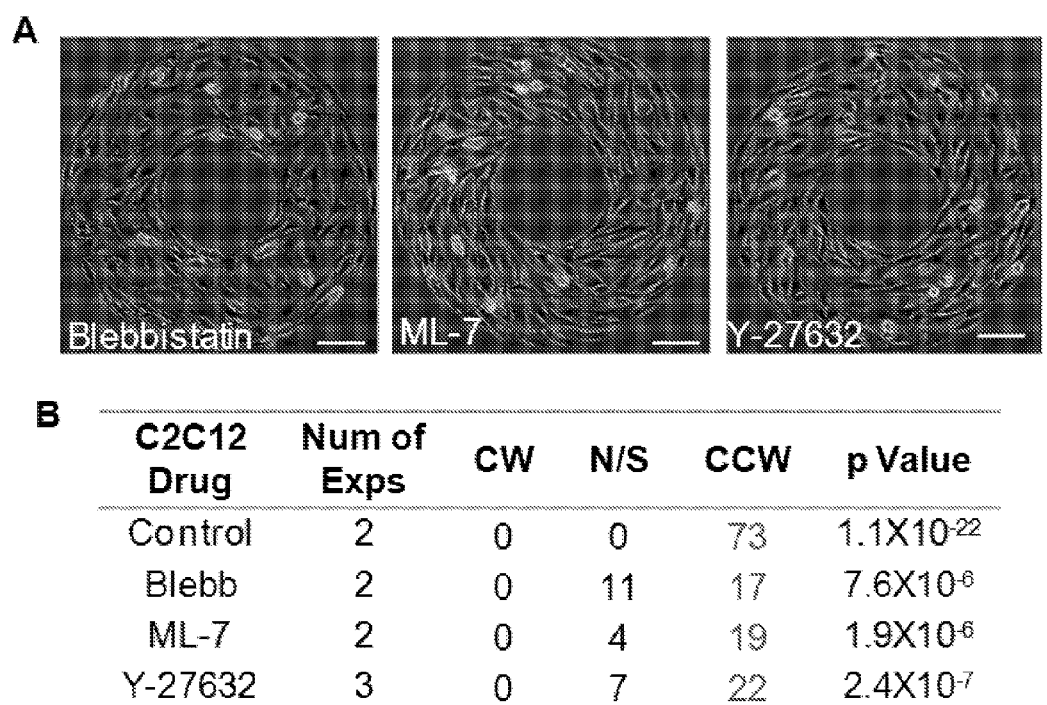
FIG. 8 is a series of phase contrast images and a table showing effects of drugs blocking the actomyosin motor. Phase contrast images (FIG. 8A) and chirality data (FIG. 8B) of C2C12 cells under the treatment of drugs that affect the function of actomyosin motor. These drugs (Blebbistatin, ML-7, and Y-27632) did not affect left-right asymmetry. Scale bars: 100 µm.

Low concentrations of the actin treadmilling inhibitors (Latrunculin A, cytochalsin D, Jasplakinolide) reversed the chirality of C2C12 cells from CCW into CW. In contrast, inhibitors of tubulin dynamics (Nocodazole, Taxol) at concentrations below those resulting in cell apoptosis did not change cell chirality. Similar results were obtained for human skeletal muscle cells (data not shown). The CCW bias of the cells depended on the function of actin but not non-muscle myosin II (see e.g., FIG. 8). In contrast to C2C12 cells, the drugs tested could not reverse the chirality of hUVEC cells or rat cardiac fibroblasts (data not shown).

Collectively, these data suggest that functional actin is required for cells exhibiting the CCW but not CW bias.

C2C12 cells treated with Latrunculin A polarized in the same fashion as the untreated cells (see e.g., FIG. 6C), as evidenced by organelle positioning relative to boundaries, suggesting that the drug did not alter cell polarization. Analysis of cell migration showed reversal at the boundaries (see e.g., FIG. 6D-E), with the cells migrating CW along the outer ring and CCW along the inner ring at 15 µm/hr.

Thus, inhibition of actin function reversed the CCW chirality and the biased migration of C2C12 cells.

Example 7

The following describes an image-processing algorithm to determine cellular chirality (left right asymmetry, handedness) on micro-patterned surfaces towards potential applications in disease detection and drug screening. The description below is for an algorithm that can be used with methods for cell, printing, cultivation and the acquisition of phase contrast images described above. The program provides automated determination of the chirality of patterned cells. Methods are according to Examples 1-5, unless specified otherwise.

A program according to Karlon W J et al, Ann Biomed Eng, 1999

The algorithm was implemented and used to determine cellular chirality from phase contrast images of cells cultured on micropatterned surfaces with well defined boundaries, according to the following sequence of steps:

1. The images of cell patterns were examined and those failing to form a perfect ring shape were excluded from further analysis.

2. For each image, the center of the ring is determined using an interactive script written in MatLab.

3. The direction of cell alignment in subregions was determined based on the fact that cell contour in phase contrast images is brighter than the interior region. In this step, the intensity gradient was determined pixel by pixel with a Gaussian differential filter. In each sub-region of the image, the dominant local direction was determined using an accumulator scheme, in which the orientation of each pixel follows a von Mises distribution, a circular analogue of the linear normal distribution.

4. The biased angle of the cell axis was then calculated for each subregion based on the deviation of cell alignment direction from the circumferential direction.

5. The cell alignment was then determined for an individual ring with Rayleigh test (analog to the Student t-test in a linear system).

6. Cell chirality was determined as the directionality of cell motion, and designated as clockwise or counterclockwise, using tens or hundreds of rings tested in from step 5.

The steps 3-6 were performed in MatLab automatically, and the program can be extended to determine cell chirality on patterned long strips (e.g., lines).

Example 8

Experiments were conducted to determine whether cancer promoters/PKC activators reverse cell chirality of human endothelial cells. Treatment groups included control; 0.9 µM Indolactam; 10 nM Phorbol 12-Myristate 13-Acetate (TPA; PMA); and 0.3 µM Phorbol 12,13-Dibutyrate.

Figure 9:
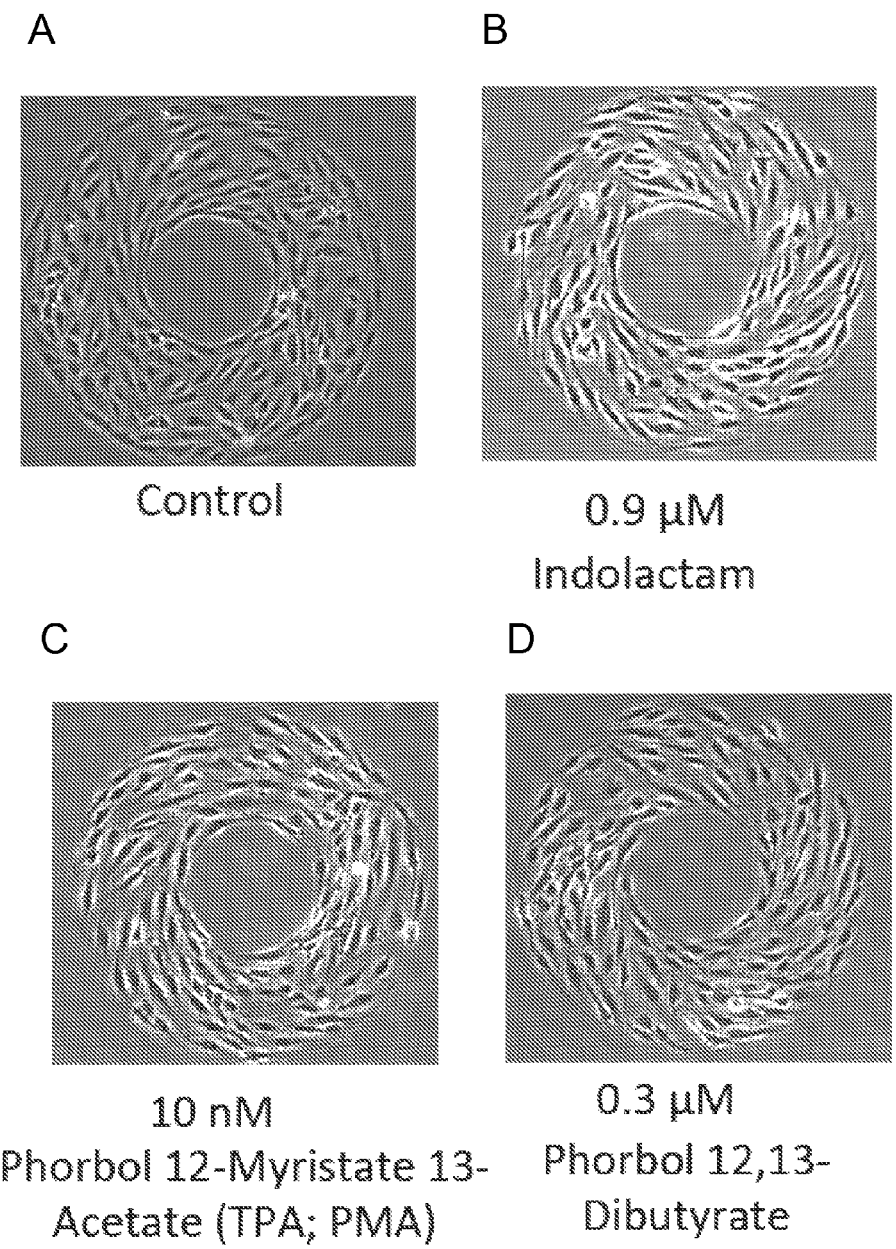
FIG. 9 is a series of phase contrast images showing effects of cancer promoters/PKC activators on chirality of human endothelial cells. Treatment groups included control (FIG. 9A); 0.9 µM Indolactam (FIG. 9B); 10 nM Phorbol 12-Myristate 13-Acetate (TPA; PMA) (FIG. 9C); and 0.3 µM Phorbol 12,13-Dibutyrate (FIG. 9D).

Results showed that the tested cancer promoters/PKC activators reverse cell chirality of human endothelial cells (see e.g., FIG. 9; compare FIG. 9A control with FIGS. 9 B, C, D). Human fibroblasts did not show similar responses in this experimental setting.

Example 9

Further experiments were conducted to characterize chirality of human primary fibroblasts, fibroblast cell line from healthy skin, and fibroblast cell line from Basal cell carcinoma.

Figure 10:
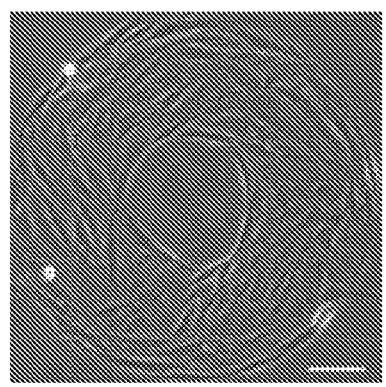
FIG. 10 is a series of phase contrast images showing chirality of human primary fibroblasts (FIG. 10A), fibroblast cell line from healthy skin (FIG. 10B), and fibroblast cell line from Basal cell carcinoma (FIG. 10C).
Figure 10:
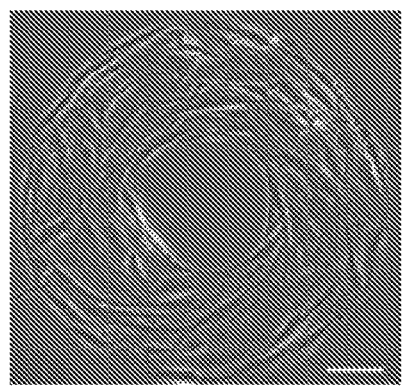
Figure 10:
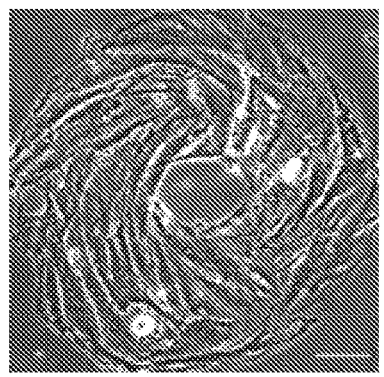

Results are shown in Table 8 and FIG. 10.

TABLE 8

Cell chirality on patterned substrates for human primary fibroblasts, fibroblast cell line from healthy skin, and fibroblast cell line from Basal cell carcinoma.

| Cell Description | Num of Exps | CW | N/S | CCW | Species | Tissue | Phenotype | Cell Culture | Catalog Number |
|---|---|---|---|---|---|---|---|---|---|
| Human primary skin fibroblast | 9 | 232 | 30 | 4 | Human | Skin | Fibroblast | Primary cells | ATCC PCS-201-012 |
| Human skin fibroblast line | 7 | 84 | 42 | 21 | Human | Skin | Fibroblast | Cell line | ATCC CRL-7761 |
| Human skin cancer fibroblast line | 6 | 48 | 61 | 110 | Human | Skin | Fibroblast | Cell line | ATCC CRL-7762 |

CW: clockwise alignment; CCW: counter-clockwise alignment; N/S: not significantly biased to CW or CCW.

Example 10

Experiments were conducted to determine chirality of cancer fibroblasts from the lung. Results are shown in TABLE 9.

TABLE 9

Cell chirality on patterned substrates for cancer fibroblasts from the lung. CW: clockwise alignment; CCW: counter-clockwise alignment; N/S: not significantly biased to CW or CCW.

| Cell Description | CW | N/S | CCW |
|---|---|---|---|
| Lung tumor line 1 | 4 | 1 | 8 |
| Lung tumor line 2 | 2 | 4 | 10 |
| Total | 6 | 5 | 18 |

The above results show that cancer fibroblasts from the lung exhibit the CCW alignment.

Example 11

Experiments were conducted to determine chirality of mutant tumorigenic cryptic mouse lines. Results are shown in TABLE 10.

TABLE 10

Cell chirality on patterned substrates for cryptic mouse lines and mutant tumorigenic cryptic mouse lines. CW: clockwise alignment; CCW: counter-clockwise alignment; N/S: not significantly biased to CW or CCW.

| Cell Description | CW | N/S | CCW |
|---|---|---|---|
| Cryptic mouse Normal | 14 | 23 | 62 |
| Cryptic mouse Mutant 1 | 51 | 15 | 4 |
| Cryptic mouse Mutant 2 | 27 | 12 | 3 |
| Cryptic mouse Mutant 3 | 80 | 28 | 11 |

The above results show that tumorigenic cryptic mouse lines exhibit CW chirality while normal cell pair exhibits CCW chirality.

Example 12

Experiments were conducted to determine whether cancer cell chirality depends on actin function. Skin cancer cells were treated with actin interfering reagent Lantrunculin A at 0 nM (control), 20 nM, 50 nM, 100 nM, or 200 nM. Results are shown in TABLE 11.

TABLE 11

Cell chirality on patterned substrates for skin tumor cancer cells in response to actin interfering reagent Lantrunculin A. CW: clockwise alignment; CCW: counter-clockwise alignment; N/S: not significantly biased to CW or CCW.

| Lantrunculin A skin tumor | CW | N/S | CCW |
|---|---|---|---|
| Control | 3 | 3 | 23 |
| 200 nM | 8 | 3 | 2 |
| 100 nM | 32 | 0 | 0 |
| 50 nM | 28 | 2 | 1 |
| 20 nM | 21 | 4 | 0 |

The above results showed that cancer cell chirality depends on actin function.

The invention claimed is:

1. A method for determining chirality of a cell comprising:
    (a) applying cells to a surface of a micropatterned substrate; wherein,
        the micropatterned substrate comprises an x-axis, a y-axis, an inner boundary, and an outer boundary, wherein the surface is disposed between the inner boundary and the outer boundary;
        the inner boundary or the outer boundary is at least partially or substantially perpendicular to the x-axis and at least partially or substantially parallel with the y-axis;
    (b) culturing the cells on the micropatterned substrate for an amount of time sufficient for a portion of the cells to contact the inner boundary or the outer boundary;
    (c) measuring an angular deviation away from the y-axis for the portion of cells, wherein the angular deviation is a positive angular deviation or a negative angular deviation, wherein the positive angular deviation is classified as a counterclockwise (CCW) alignment and the negative angular deviation is classified as a clockwise (CW) alignment, and wherein the CCW alignment and CW alignment denotes the chirality of the portion of the cells.

2. The method of claim 1, wherein the cells comprise a density of about 2,000 cells $cm^{-2}$ to about 500,000 cells $cm^{-2}$.

3. The method of claim 1, wherein the substrate micropattern comprises a ring or linear strip geometrical shape.

4. The method of claim 1, wherein the substrate micropattern comprises a ring having an inner diameter of from about 150 μm to about 350 μm, and wherein the substrate micropattern comprises a distance of from about 100 μm to about 300 μm along the x-axis between the inner boundary and the outer boundary.

5. The method of claim 1, wherein the positive angular deviation is from about 2 degrees to about 15 degrees in the CCW direction, and wherein the negative angular deviation is from about 2 degrees to about 15 degrees in the CW direction.

6. The method of claim 1, wherein measuring the angular deviation comprises phase contrast imaging of the portion of cells.

* * * * *